(12) United States Patent
Campbell et al.

(10) Patent No.: US 7,198,753 B1
(45) Date of Patent: Apr. 3, 2007

(54) SYSTEM AND METHOD FOR MONITORING AND/OR CONTROLLING ATTRIBUTES OF MULTIPLE CHEMICAL MIXTURES WITH A SINGLE SENSOR

(75) Inventors: Mark A. Campbell, Bastrop, TX (US); Phuong-Anh Tang, Austin, TX (US); Gary R. Anderson, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 808 days.

(21) Appl. No.: 09/366,441

(22) Filed: Aug. 3, 1999

(51) Int. Cl.
*G01N 30/00* (2006.01)

(52) U.S. Cl. .................... 422/68.1; 422/81; 422/100; 422/102; 436/180

(58) Field of Classification Search ............... 422/68.1, 422/81, 83.05, 100; 436/164
See application file for complete search history.

(56) References Cited

U.S. PATENT DOCUMENTS

| | | |
|---|---|---|
| 4,722,830 A | 2/1988 | Urie et al. |
| 5,783,740 A | 7/1998 | Tawarayama et al. |

FOREIGN PATENT DOCUMENTS

EP          0 543 544          5/1993

OTHER PUBLICATIONS

Horiba Bulletin HRA-1883A re: SC-1 Monitor, CS-200 Series.
Horiba Bulletin HRE-0007J entitled "Products for Semiconductor Industry."
Z-World Products and Services re: OP7100, 3 pgs., printed May 24, 1999.
Z-World Products and Services re: PK2200, 3 pgs., printed May 24, 1999.
Z-World Products and Services re: XP8100, 2 pgs., printed May 24, 1999.
Z-World Products and Services re: XP8500, 1 pg., printed Jun. 3, 1999.
Z-World Products and Services re: XP8700, 1 pg., printed May 24, 1999.

*Primary Examiner*—Jill Warden
(74) *Attorney, Agent, or Firm*—Robert C. Kowert; Meyertons, Hood, Kivlin, Kowert & Goetzel, P.c.

(57) ABSTRACT

A monitoring system is presented. The monitoring system may include a first chemical vessel containing a first chemical mixture and a second chemical vessel containing a second chemical mixture. The monitoring system may further include a sensor configured to selectively receive a first sample flow of the first chemical mixture from the first chemical vessel and a second sample flow of the second chemical mixture from the second chemical vessel. The sensor may be configured to measure a first sample attribute value of the first sample flow and a second sample attribute value of the second sample flow. By multiplexing multiple sample flows through a sensor, the monitoring system may monitor attributes of multiple chemical mixtures without requiring separate sensors for each chemical mixture monitored by the system.

In an embodiment, the monitoring system is preferably configured to control an attribute of a chemical mixture. In such a case, the monitoring system may further include a control system configured to receive the first sample attribute value and the second sample attribute value from the sensor. The control system is further preferably configured to input the first sample attribute value into a first attribute control algorithm to calculate a first attribute control output. The first chemical mixture includes a first bulk attribute value, and the control system is preferably configured to direct the adjusting of the first bulk attribute value.

13 Claims, 22 Drawing Sheets

SYSTEM AND METHOD FOR MONITORING AND/OR CONTROLLING ATTRIBUTES OF MULTIPLE CHEMICAL MIXTURES WITH A SINGLE SENSOR

BACKGROUND OF THE INVENTION

1. Field of the Invention

This invention relates to chemical processing and, more particularly, to systems and methods for monitoring attributes of multiple chemical mixtures using a single sensor, and further to systems and methods for controlling attributes of multiple chemical mixtures monitored by a single sensor, the systems and methods being especially configured for use in semiconductor processing.

2. Description of the Related Art

The information described below is not admitted to be prior art by virtue of its inclusion in this Background section.

There is much that separates the wide variety of activities that constitute the field of chemical processing. One common thread between chemical processes, however, is the extent to which variations in the attribute values of the chemical mixtures used in these processes can influence process outcomes. Chemical processes are typically designed on the assumption that values of chemical mixture attributes (e.g., temperature, concentration, particle count, and resistivity) can be maintained within predetermined ranges during processing. In many cases, these processes may be further designed on predictions of how chemical mixture attributes will vary within such ranges over time. Generally speaking, the success of a chemical process is dependent on how closely chemical mixture attributes can be maintained to ideal levels, with the degree of closeness necessary for success varying from industry to industry and from process to process. If, however, result-effective chemical mixture attributes are allowed to fall outside of predetermined ranges, a chemical process will often fail to achieve its goals.

One field of chemical processing where the importance of the above can be seen is in semiconductor processing. Chemical mixtures are used in a variety of ways in semiconductor processing, and play a particularly important role in etching and cleaning processes. Of the cleaning processes used in semiconductor processing, one of the most prevalent is the standard clean 1 (SC1) cleaning process. SC1 clean is the first step of the traditional RCA clean. SC1 solutions are solutions of water, hydrogen peroxide ($H_2O_2$), and ammonium hydroxide ($NH_4OH$) (in order of decreasing typical concentration), and are often heated to between 60 and 85° C. during use. SC1 solutions may additionally include other chemicals, such as chelating agents used to bind up metallic ions present in the solution.

The SC1 clean may be used to remove residual organic and metallic contaminants that remain after various processing steps. For example, SC1 solutions are often used to remove residue remaining from chemical-mechanical polishing (CMP) procedures. CMP procedures are considered "dirty" procedures, and as such a great deal of residue often remains on wafer surfaces after such processes are complete. SC1 cleans may be used to remove this residue, reducing the defect probability in the finished product. In a typical post-CMP cleaning sequence, the wafers to be cleaned are immersed in a SC1 solution bath for a specified time to remove residue remaining from the CMP process. Alternately, spray-cleaning methods incorporating SC1 solutions may be used to clean the wafers.

When using SC1 solutions to clean silicon-bearing surfaces (e.g., a single-crystal silicon wafer and any polysilicon deposited thereupon), however, care must be taken to maintain concentrations of the component chemicals within certain values. While a properly balanced SC1 solution will not remove an inordinate amount of the silicon during cleaning, silicon surfaces can suffer chemical attack if concentrations deviate too severely from desired ranges during processing. For example, ammonium hydroxide will, in the absence of hydrogen peroxide, etch silicon. To avoid undesirable attack of silicon surfaces, it is important to maintain hydrogen peroxide concentration values within a SC1 solution at sufficiently high levels during processing.

Unfortunately, the hydrogen peroxide within an SC1 solution often decomposes over time. Such decomposition can occur, for example, as the result of impurities accumulating within the solution or if the solution temperature rises too far above desired levels. If an SC1 solution is used in which sufficient hydrogen peroxide is not present, the ammonium hydroxide can severely attack silicon surfaces, possibly reducing polysilicon feature sizes beyond acceptable levels or etching the wafer backside in such a way that problems are created further along in the manufacturing sequence. As linewidths reach 0.15 microns and below, it becomes even more important to maintain the component concentrations of an SC1 solution within acceptable ranges.

To prevent the occurrence of such undesirable situations, the concentration and other attributes of chemical solutions used in semiconductor processing have historically been checked using various qualification processes. Qualification processes attempt to characterize various parameters of a process, such as how solution properties change with continued use over time. For example, in one type of qualification process a series of test wafers may be sequentially sent through a chemical bath to determine how long the bath can be used in processing before one or more chemical concentrations (or other attributes) of the cleaning solution within the bath fall outside of acceptable ranges. From the data obtained in such a qualification process, the bath life may be estimated, and the overall cleaning sequence can be adjusted accordingly. However, such characterization techniques only estimate concentration from historical data, and as such are not always sensitive to the variations that may occur from run-to-run. In addition, when qualification wafers are being run through a process production wafers are not, so the extensive qualification of a process can reduce the total amount of time that process is available for use on production wafers.

In addition, other events often arise during processing for which qualifying processes are inadequate means of prevention. For example, chemical solutions used in semiconductor processing are often mixed from separate sources in a single tank during a process called pour-up. In a typical design, metering pumps are used to supply each constituent chemical of the solution being poured-up. The tanks also may include capacitive sensors to detect solution levels and control the balance of deionized water for pour-ups. In such configurations, the pour-up process may be an automated process that utilizes the metering pumps and capacitive sensors to mix a solution at a desired concentration. If not all the components of the pour-up system are operating optimally, however, bad pour-ups (i.e., situations in which the solution concentrations after pour-up are not at desired levels), can sometimes result. Even worse, one or more of these metering pumps can, from time to time, suffer total failure. Such metering pump failure may result in the chemical supplied from the failed metering pump being absent altogether from the final solution. What's more, metering pump failures are often not immediately detected, and may escape notice until the next qualification process is run. Processing a wafer with such an improperly balanced solution can cause irreversible damage, and if gone undetected, can even result in the loss of several lots of production wafers.

To avoid such problems, some manufacturers have resorted to placing concentration sensors on each tank supplying process chemicals to ensure that solution concentrations are within acceptable levels before the solutions are used in the processing of production wafers. Unfortunately, the concentration sensors required to reach desired accuracy levels are expensive, often costing $50,000 dollars or more. Furthermore, such sensors typically need to be rigorously maintained, further increasing their associated cost of ownership. In many cases, the cost of installing and maintaining concentration sensors on every chemical mixture that would profit from monitored outweighs the benefits obtained from concentration monitoring. Consequently, concentration monitoring may only be implemented in select tanks or forgone entirely.

Therefore, it would be desirable to design a monitoring system capable of monitoring an attribute (e.g., concentration) of multiple chemical mixtures within multiple chemical vessels during processing that did not require a separate concentration sensor for each chemical vessel being monitored.

SUMMARY

The problems described above are in large part resolved by a monitoring system as described herein. The monitoring system may include a first chemical vessel containing a first chemical mixture and a second chemical vessel containing a second chemical mixture. The monitoring system may further include a sensor configured to selectively receive a first sample flow of the first chemical mixture from the first chemical vessel and a second sample flow of the second chemical mixture from the second chemical vessel. The sensor may be configured to measure a first sample attribute value of the first sample flow and a second sample attribute value of the second sample flow. By multiplexing multiple sample flows through a sensor, the monitoring system may monitor attributes of multiple chemical mixtures without requiring separate sensors for each chemical mixture monitored by the system.

A monitoring system as described herein may have numerous benefits. For example, the monitoring system may be less expensive than conventional monitoring systems. Because the monitoring system can use a single sensor to monitor multiple chemical mixtures, fewer sensors may need to be purchased than in systems with dedicated sensors for each chemical mixture monitored. And since the present monitoring system may have fewer sensors than conventional monitoring systems, sensor maintenance expenses may be lower than in conventional systems.

In addition, the present monitoring system may posses dimensional benefits over conventional monitoring systems. Processing areas within semiconductor fabrication facilities ("fabs") must be kept free of particulates and other contaminants. The cost of providing the clean rooms used to reduce contamination is high, and thus the total amount of space available for production equipment in a fab is limited. As stated above, the present system preferably does not use a dedicated sensor for each chemical mixture monitored. Consequently, the overall sensor footprint of the present monitoring system may be significantly less than that of conventional monitoring systems, potentially saving valuable production space.

The monitoring system may be configured to monitor one or more attributes of any number of chemical mixtures. Elements of the monitoring system and operated on by the monitoring and associated with a given chemical mixture may be described with an ordinal number corresponding to an ordinal number of their associated chemical mixture. For example, a sample flow from the second chemical mixture may be a second sample flow, and a chemical vessel containing a third chemical mixture may be a third chemical vessel. For the purposes of this disclosure, the term nth, when added to a term such as chemical mixture, chemical vessel, or sample flow, may refer to any particular ordinal number of a system component, and will often be used herein to describe the particular group of associated components (e.g., chemical mixture, sample flow, chemical vessel) that is currently under measurement and/or being transported to or from a sensor.

Additionally, attribute monitoring of each chemical mixture is preferably performed sequentially. That is, a sample flow of one chemical mixture is transported to a sensor for a certain length of time and then a sample flow of another chemical mixture is transported to the sensor for a certain length of time. Purge fluid may be transported through the system, including the sensor, between measurement sequences to aid in obtaining measurements that are more accurate. In addition, a sample flow may be transported through the sensor and to a drain for a period before measuring begins for similar purposes. Such processes may also aid in preventing the undesired transport of chemicals from one chemical mixture into another chemical mixture. Since the monitoring system preferably monitors similar chemical mixtures, it may be unnecessary to purge to the point of zero contamination. As such, the time between measurement sequences of different sample flows may be reduced.

It is understood that the transporting of sample flows from multiple chemical vessels into a single, preferably centrally located sensor may produce a slightly increased delay in measurement response time when compared to a system having sensors dedicated to each chemical vessel. Consequently, the monitoring system is preferably configured such that substantially all system-induced error is reduced. In a preferred embodiment, the error between a measured sample attribute value and an actual bulk attribute value is within analytical error. That is, the above-described error is preferably substantially equal to the equivalent error of a similarly configured sensor that of a sensor that solely monitors a particular chemical mixture.

In addition, the monitoring system preferably has a sample time sufficiently short to allow it to detect changes in an attribute value of a chemical mixture before those changes become sufficiently large. The sample time of monitoring system may be the time required to transport a sample flow to the sensor, measure an attribute value of the sensor with the sample flow, transmit the measured attribute value to another device for reporting (e.g., a control system), and prepare to accept a sample flow from a subsequent chemical mixture. While the present monitoring system may not measure attributes of all chemical mixtures being monitored simultaneously, the sample time of the monitoring system is preferably such that each chemical mixture may be monitored with a frequency sufficient to detect changes in the monitored attribute values before the attribute values reach dangerous levels.

Furthermore, the sample time of the monitoring system for a given chemical mixture being monitored is preferably sufficiently short that after pour-up of a chemical mixture begins, the monitoring system may return to the vessel in which the mixture will be contained before that mixture is used in processing. As stated above, problems such as bad pour-up or metering pump may from occur periodically, and in unmonitored systems these problems may escape detection and cause serious damage to the production wafers. The present monitoring system, however, preferably has a cycle time sufficiently short to prevent these problems before the affected chemical mixtures are used in processing. The monitoring system may preferably detect changes in attribute values of a chemical mixture both within a run and from run-to-run.

Preferably, the sensor is a concentration sensor. In such a situation, the first sample attribute may be a first sample concentration of a first sample flow and the second sample attribute may be a second sample concentration of a second sample flow. The first and second sample flow may be liquids. The sensor is further preferably configured to measure a plurality of sample attributes of a sample flow. For example, the sensor may be configured to measure concentrations of all the chemical components of a sample flow, as well as other attributes such as temperature or resistivity. The ability to monitor multiple attributes of a sample flow may allow for a more accurate reading of one or more of the attributes measured to be reported. For example, the ability to measure solution temperature may allow for more accurate sample flow chemical component concentrations to be reported by the sensor or to be calculated by other components of the monitoring system.

Monitoring of chemical mixture attributes allows for improved process characterization. For example, by monitoring the concentration and temperature of a chemical mixture, the etch rate of that mixture at a particular instant may be determined. That information can be use to calculate the etch rate of a mixture at present conditions. Consequently, the length of a process may be adjusted before and/or during the process as necessary.

The monitoring system may further include a supply distribution system configured to selectively transport the first and second sample flow to the sensor. The supply distribution system is preferably configured to transport the first and second sample flow to the sensor at a substantially constant flow rate during operation.

The monitoring system may further include a purge fluid supply and a drain configured to receive fluids. The supply distribution system is preferably configured to selectively transport the purge fluid flow from the purge fluid supply to the sensor. Preferably, the monitoring system further includes a return distribution system. The return distribution system is preferably configured to transport purge fluids from the sensor to the drain. Additionally, the return distribution system may be configured to transport a sample flow back to its respective chemical vessel or to the drain.

Furthermore, the monitoring system preferably comprises a control system. The control system is preferably configured to interface with the various components of the monitoring system to direct the monitoring process. As such, the control system may be considered to provide "intelligence" for the monitoring system. The control system is preferably configured to receive measured sample attribute values from the sensor. The control system may include a display unit configured to display the measured attribute values.

The control system is preferably also configured to direct the operation of the supply distribution system and the return distribution system. By transmitting appropriate signals to components of the supply and return distribution systems, the control system is preferably capable of selecting which flows are to be transported to and from the sensor.

Additionally, the actions of the monitoring system are preferably at least partially directed through software. The software instructions may be at least temporarily stored in a storage element of the control system. The storage element may be any type of media configured to store, if only temporarily, several groupings of instructions for carrying out several processing steps.

An embodiment is directed to processing steps by which programming instructions, preferably residing in the storage element, may be executed by the control system to direct the operation of components of the monitoring system. The processing steps include executing a monitoring process on an nth chemical mixture (nth is preferably an ordinal number). The monitoring process may be initially executed for nth="first". Executing a monitoring process preferably includes executing a measurement process on the nth chemical mixture.

Before executing a measurement process, the monitoring process may include processing steps for executing an equipment readiness verification process and for executing a dump flow process. After executing a measurement process, the monitoring process may include processing steps for executing a purge flow process. After a monitoring process as been executed for the first chemical vessel, the execution of the monitoring process may be repeated for a second chemical mixture, a third chemical mixture, a fourth chemical mixture, etc., until the process has been repeated for all chemical mixtures being monitored by the monitoring system (however, it is not required to repeat the steps in any particular order).

An embodiment is directed to a monitoring process. Execution of the monitoring process preferably directs at least a portion of the performance of the monitoring process. The monitoring process preferably involves providing a sensor configured to measure an attribute of a chemical mixture, a first chemical vessel containing a first chemical mixture, and a second chemical vessel containing a second chemical mixture. The monitoring process also preferably includes performing a monitoring sequence on an nth sample attribute of an nth sample flow of the nth chemical mixture, wherein nth is an ordinal number, and wherein said performing a monitoring sequence comprises performing the monitoring sequence for nth="first", said performing a monitoring sequence further comprising: performing a measurement sequence, said performing a measurement sequence comprising transporting the nth sample flow of the nth chemical mixture from the nth chemical vessel to the sensor; and measuring an nth sample attribute of the nth sample flow with the sensor for producing an nth sample attribute value; and repeating said performing a monitoring sequence on an nth sample attribute for nth="second".

In addition to the ability to monitor one or more attributes of multiple chemical mixtures, monitoring systems as described herein may also employ a variety of process control techniques. Process control techniques may involve using the value of a monitored attribute to determine the extent to which one or more manipulated variables are manipulated to, e.g., adjust the monitored attribute toward a setpoint value (i.e., a desired value). In such a case, the monitored attribute may be considered a controlled attribute. Generally speaking, process control techniques may be implemented in monitoring systems as described herein by inputting one or more measured sample attribute values into a control algorithm. The control algorithm may be used to generate a control output, which may in turn be used to determine the extent of actions taken by the monitoring system on a manipulated variable. The particular value of the control output may determine the extent to which a manipulated variable is manipulated, or whether the manipulated variable will be manipulated at all. Various process control techniques may be used to control attributes monitored by monitoring systems of the present disclosure. The particular control techniques used may in large part depend on the particular attribute being monitored.

In an embodiment, the monitoring system includes a first chemical vessel containing a first chemical mixture and a second chemical vessel containing a second chemical mixture. The monitoring system may further include a sensor configured to selectively receive a first sample flow of the first chemical mixture and a second sample flow of the second chemical mixture from the second chemical vessel. The sensor may be configured to measure a first sample attribute value of the first sample flow and a second sample attribute value of the second sample flow. The monitoring system preferably further includes a control system configured to receive the first sample attribute value and the second sample attribute value from the sensor. The control system is further preferably configured to input the first sample attribute value into a first attribute control algorithm to calculate a first attribute control output. The first chemical mixture includes a first bulk attribute value, and the control system is preferably configured to direct the adjusting of the first bulk attribute value.

BRIEF DESCRIPTION OF THE DRAWINGS

Other objects and advantages of the invention will become apparent upon reading the following detailed description and upon reference to the accompanying drawings in which.

Figure 1:
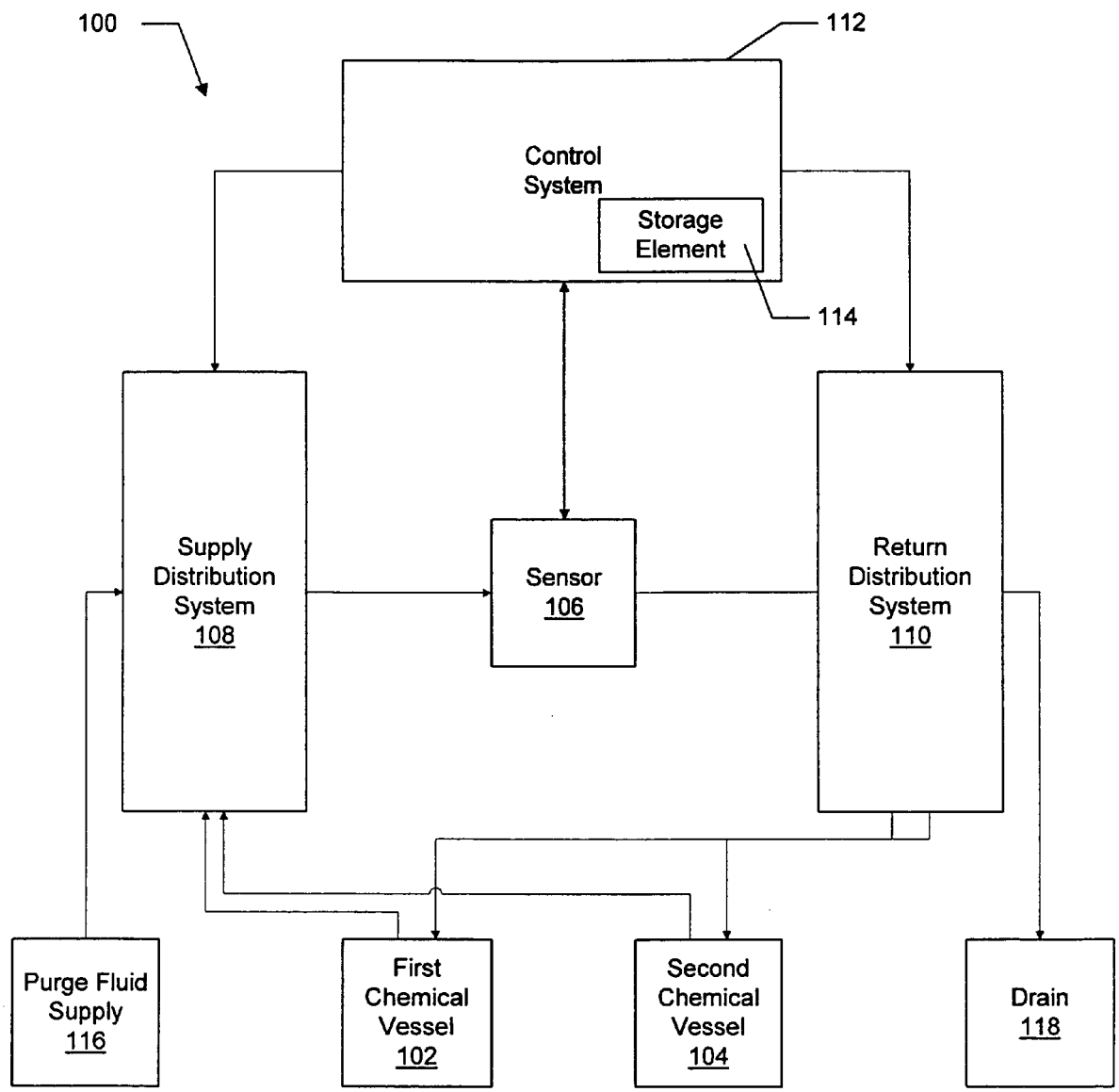
FIG. 1 is a schematic view of a monitoring system in accordance with an embodiment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Referring now to the Drawings, FIG. 1 presents monitoring system 100. Monitoring system 100 is preferably configured to monitor one or more attributes of multiple chemical mixtures contained in multiple chemical vessels. In the embodiment shown in FIG. 1, monitoring system 100 includes a first chemical vessel 102 and a second chemical vessel 104. First chemical vessel 102 preferably contains a first chemical mixture. Likewise, second chemical vessel 104 preferably contains a second chemical mixture. In addition, monitoring system 100 preferably includes sensor 106. Sensor 106 is preferably configured to selectively receive a first sample flow of the first chemical mixture from the first chemical vessel and to selectively receive a second sample flow of the second chemical mixture from the second chemical vessel. Stated otherwise, sensor 108 is preferably configured within monitoring system 100 such that, during operation, sensor 106 may selectively receive sample flows from the first and second chemical vessels. Preferably, sensor 106 is configured to measure a first sample attribute of the first sample flow and a second sample attribute of the second sample flow. By multiplexing multiple sample flows through sensor 106, monitoring system 100 may monitor attributes of multiple chemical mixtures without having to use separate sensors for each chemical mixture monitored.

First chemical vessel 102 and second chemical vessel 104 may be any of a variety of vessels capable of containing the first and second chemical mixtures. For example, first and second chemical vessels 102 and 104 may be chemically inactive receptacles capable of containing acids or other reactive solutions for use in etching, cleaning, or stripping wafers (e.g., acid tanks). First and second chemical vessels 102 and 104 may be used to hold chemicals for use in a separate chamber. For example, the chemical vessels could store chemicals to be used in a distally located processing tool. In such a case, first and second chemical vessels 102 and 104 may both supply the same processing tool, or may each supply different processing tools. Alternately, the first and second chemical vessels can themselves be configured to process and/or react with materials placed therein (e.g., the chemical vessels could be baths into which semiconductor substrates are dipped for cleaning).

The first and second chemical mixtures within first and second chemical vessels 102 and 104, respectively, may be any of the variety capable of having an attribute measured by a sensor. The first and second chemical mixtures may be in any physical state or combination of states. When at desired levels, the first and second chemical mixtures are preferably substantially the same mixture (i.e., they contain substantially the same chemicals at substantially the same concentrations). For example, the first and second chemical mixtures may both be SC1 solutions. However, the first and second chemical mixture may contain entirely different components. Preferably, the first and second mixtures contain at least a first chemical and a second chemical. The terms "first" or "second" chemicals are not required to refer to any chemicals in particular within a chemical mixture; in an embodiment in which the first and second mixtures are SC1 solutions, the first and second chemicals may be considered to be any one of hydrogen peroxide, ammonium hydroxide, or water.

Sensor 106 may be part of a larger sampling subsystem including all components of monitoring system 100 configured to selectively transport fluid flow to the sensor, measure one or more fluid flow attributes (if desired), and transport fluid flow away from the sensor (components of the sampling subsystem may be further configured to perform numerous functions other than and outside of the scope of those mentioned above). As part of the sampling subsystem, monitoring system 100 further preferably includes supply distribution system 108 and return distribution system 110.

Supply distribution system 108 is preferably arranged upstream of sensor 106. Supply distribution system 108 is preferably configured to selectively transport fluid flow from various locations (e.g., the first and second chemical vessels) to sensor 106. Supply distribution system 108 is preferably configured to selectively transport the first sample flow of the first chemical mixture from first chemical vessel 102 to sensor 106. Supply distribution system 108 is preferably further configured to selectively transport the second sample flow of the first chemical mixture from second chemical vessel 104 to sensor 106. A sample flow may be a flow of a chemical mixture that is transported to a sensor and having one or more attributes thereof measurable by the sensor. The measured attribute or attributes of a sample flow measured by the sensor may be considered sample attributes, and the values of the sample attributes may be considered sample attribute values. As will be explained below, sample attribute values measured by sensor 106 are preferably representative of bulk attribute values of a respective chemical mixture within a respective chemical vessel at the time the sample attribute values are measured by sensor 106. Supply distribution system 108 preferably includes numerous fluid flow paths in fluid communication with the first and second chemical vessels and a supply manifold configured to allow fluid flow to be transported only from selected chemical vessels. A supply manifold within supply distribution system 108 may include numerous valves such as solenoid valves configured to be actuated by a central control system. The valves within supply distribution system 108 may be selectively actuated to selectively place first chemical vessel 102 or second chemical vessel 104 in fluid communication with sensor 106. As a result of these features, supply distribution system 108 may be viewed as a multiplexor, in that it may be configured to multiplex several signals (i.e., sample flows) over a single line (e.g., a supply flow line from a supply manifold to sensor 106).

Supply distribution system 108 may also include one or more pumps to aid in transporting fluid flow to sensor 106. Supply distribution system 108 is also preferably configured to prevent the backflow of fluid flow that has entered the supply distribution system (e.g., by incorporating check valves). Furthermore, supply distribution system is preferably configured to transport a sample flow to the sensor at a substantially constant flow rate during operation. Consequently, supply distribution system 108 preferably aids in eliminating flow rate induced measurement variation, and thus allows monitoring system 100 to more accurately measure the attributes of the sample flows passing through sensor 106.

Return distribution system 110 is preferably arranged downstream of sensor 106. Return distribution system 110 is preferably configured to selectively transport fluid flow from sensor 106 to other locations. Return distribution system 110 preferably includes a return flow line from the sensor to a return manifold. Furthermore, return distribution system 110 preferably includes numerous fluid flow paths configured to be in fluid communication with the first and second chemical vessels. During operation, return distribution system 110 is preferably configured to return the first supply flow to the first chemical vessel and the second supply flow to the second chemical vessel. As such, return distribution system 110 preferably allows for recirculation of a sample flow to the chemical vessel from which it originated after the sample flow has been measured by the sensor. Return distribution system 110 may include filters for filtering sample flows before the sample flows are transported back to their respective chemical vessels. Additionally, monitoring system 100 may include filters in other areas of the monitoring system. Return distribution system 110 may be viewed as a demultiplexor, in that the system may be configured to separate multiplexed signals (i.e., sample flows) from a single line and transport them to various locations.

It should also be understood that neither supply distribution system 108 nor return distribution system 110 need be confined to any one area of monitoring system 100. Each system may include multiple components distally arranged throughout monitoring system 100. In another embodiment, each system may be contained in one central location, and the systems may even be combined as one contiguous distribution system.

Monitoring system 100 preferably also includes purge fluid supply 116. Purge fluid supply 116 preferably is configured to supply purge fluids for purging system 100 after one or more sample flows has been transported therethrough. Purge fluid supply 116 may be configured to supply a purge gas and/or a purge fluid. The purge gas is preferably an inert gas, and more preferably nitrogen (N2). The purge fluid may be deionized water. Preferably, purge fluid supply 116 is configured to be in fluid communication with supply distribution system 108. Supply distribution system 108 is preferably configured to selectively transport a purge fluid flow from the purge fluid supply to sensor 106. Purge fluids supplied from purge fluid supply 116 preferably have enough head to travel to sensor 106 and further to drain 218 without any pumping assistance from supply distribution system 208.

Monitoring system 100 preferably also includes drain 118. Drain 118 is preferably configured to receive fluid flow from sensor 106 that is, e.g., desired to be disposed of or recycled. If it is not desired to recycle a sample flow back to its original vessel, return distribution system 110 is further preferably capable of transporting the sample flow to drain 118. In an embodiment, return distribution system 110 is preferably configured to selectively transport a first sample flow from sensor 106 to first chemical vessel 102 or to drain 118 and to selectively transport a second sample flow from sensor 106 to second chemical vessel 104 or to drain 118. Drain 118 may not necessarily be a physical storage area, but may represent a fluid flow path away from monitoring system 100 and toward, e.g., an area of a fab where chemicals are processed for disposal and/or reuse.

Sensor 106 may be any of a variety of devices configured to measure an attribute of chemical mixture. As stated above, an attribute of a chemical mixture may be any measurable quality of the chemical mixture. Preferably, sensor 106 is configured to measure an attribute of a chemical mixture and transmit a signal representing a value of that attribute to another device (e.g., a control system). The first chemical mixture within first chemical vessel 102 preferably has a first bulk attribute. A bulk attribute may be considered an attribute possessed by an entire chemical mixture. For example, first bulk attributes of the first chemical mixture may include a bulk chemical concentration within the entire first chemical mixture, a bulk resistivity of the entire first chemical mixture, or a bulk temperature of the entire first chemical mixture.

Monitoring system 100 is preferably configured such that a first sample attribute value measured by sensor 106 is representative of a first bulk attribute value of the first chemical mixture when the first sample attribute value is measured by sensor 106. A sample attribute value may be considered representative of a bulk attribute value when the error between the sample attribute value and the bulk attribute values is within analytical error. That is, the error between a representative sample attribute value and a bulk attribute value is preferably not substantially greater than the error would be if a sensor dedicated to the chemical mixture was measuring the bulk attribute value. Likewise, the second chemical mixture within second chemical vessel 104 preferably has a second bulk attribute. A second sample attribute value measured by the sensor is preferably representative of a second bulk attribute value within the second chemical mixture at the time the second sample attribute value is measured by sensor 106.

While it was mentioned above that sensor 106 may be a concentration sensor, sensor 106 may also be configured to measure a variety of other properties of a chemical mixture. In fact, sensor 106 may be configured for use in a variety of applications, including liquid concentration measurement, gas concentration measurement, particle characterization, gas delivery control, plasma monitoring and diagnosis, and x-ray detection. Sensor 106 may also use a variety of techniques for accomplishing such goals, including: x-ray detection, spectrometric techniques (e.g., IR/UV), optical techniques (e.g., light scattering, diffraction, counting), IR detection and IR filtering, screen image enhancement techniques (e.g., NDIR), mass flow control, x-ray beam-condensing techniques, near-infrared spectrophotometry, electrochemical measurement, and Raman spectroscopy. Exemplary sensor types will be described in more detail below. However, the applications and techniques of sensor 106 described herein should not be considered a restrictive listing; other applications for sensor 106 and techniques for configuring sensor 106 may be apparent to those skilled in the art having the benefit of this disclosure.

In an embodiment, sensor 106 is a concentration sensor configured to measure concentration. Consequently, the first sample attribute may be a first sample concentration of a first chemical within the first sample flow. Likewise, the second sample attribute may be a second sample concentration of the first chemical within the second sample flow. The first sample flow and second sample flow are preferably the same state as the chemical mixture they originated from, and thus may be in, e.g., liquid, solid, gaseous, or plasma form, and combinations thereof. A sensor 106 configured as a concentration sensor is preferably further configured for the particular state of the sample flows that it measures, and may also be configured for optimal measurement of the particular chemicals contained within the sample flows. In an embodiment, sensor 106 may be configured as an absorptiometer configured to use absorption spectroscopy to measure concentrations within a sample flow.

If the chemical mixtures from which sample flows will be taken for measurement by sensor 106 are SC1 solutions (i.e., certain mixtures of water, hydrogen peroxide, and ammonium hydroxide), then sensor 106 is preferably a sensor particularly configured to measure concentrations of SC1 solutions, such as the Horiba CS220 SC-1 monitor, commercially available from the Horiba Group, Minami-ku, Kyoto, Japan. If the chemical mixtures from which sample flows will be taken for measurement by sensor 106 are SC2 solutions (i.e., certain mixtures of water, hydrogen peroxide, and hydrochloric acid), then sensor 106 is preferably a sensor configured to measure concentrations of SC2 solutions, such as the Horiba CS-342 SC-2 monitor. Sensor 106 may also be a sensor particularly configured to measure concentrations of any number of other liquid solutions, including, but not limited to, SPM (i.e., certain mixtures of water, hydrogen peroxide, and sulfuric acid), FPM (i.e., certain mixtures of water, hydrogen peroxide, and hydrofluoric acid), and hydrofluoric acid solutions.

Sensor 106 may be further configured to measure gas concentrations. A sensor 106 configured to measure gas concentration may be a residual gas analyzer. A suitable gas concentration sensor may be the Horiba IR-100. Sensor 106 may also be configured as a liquid particle counter. Attributes measurable by such a sensor include particle type, number, and diameter. Suitable liquid particle counters may include the Horiba PLCA-310, 311, 700, and 800 models. Sensor 106 may be configured to measure resistivity of a chemical mixture. For example, sensor 106 may be configured to measure the resistivity of isopropyl alcohol solutions. A suitable sensor may be the Horiba IP-960 monitor. Sensor 106 may also be configured to measure glow discharge/plasma attributes, such as electron number, ion density, and ion energy. A suitable sensor includes the DIGIPROBE, commercially available from the Horiba Group.

Sensor 106 preferably uses no physical catalysts such as electrodes or reagents, allowing sample flows to be returned to their original vessels with no waste product be dealt with. Sensor 106 further preferably has a relatively high repeatability. For example, sensor 106 may have a repeatability of less than 0.1 wt. %. Furthermore, sensor 106 is preferably configured to have a relatively short sample time (i.e., the time required for the sensor to measure an attribute of a sample flow). Sensor 106 may be configured to have a sample time of less than one minute, and more preferably may be configured have a sample time of 20 seconds or less. A shorter sample time preferably allows for a greater number of measurements to be received during a particular measurement cycle, and can increase the accuracy of the measured value reported. Whatever type of sensor is used, the preferences for high repeatability, short sample time, and other properties of sensor 106 preferably hold true. However, it is recognized that such goals may not be attainable with all sensor types.

Sensor 106 is further preferably configured to measure a plurality of sample attributes of a sample flow. For example, sensor 106 may be configured to measure concentrations of all the chemical components of a sample flow, as well as other attributes such as temperature or resistivity. In an embodiment in which first and second chemical mixtures are configured as SC1 solutions, the sensor is preferably configured to measure the solution temperature as well as the respective concentrations of ammonia hydroxide, hydrogen peroxide, water, and any other chemicals present. Additionally, multiple sensors may be used to measure multiple attributes of a sample flow. The ability to monitor multiple attributes of a sample flow may allow for a more accurate reading of one or more of the attributes measured to be reported. For example, the ability to measure solution temperature may allow for more accurate concentrations of the sample flow chemical components to be reported by sensor 106 or to be calculated by other components of monitoring system 100.

Monitoring system 100 also preferably includes control system 112. Control system 112 is preferably configured to interface with the various components of monitoring system 100 to direct the monitoring process. As such, control system 112 may be considered to provide "intelligence" for monitoring system 100. The functions of control system 112 need not be performed by a single device; rather, control system 112 may include numerous components configured to interface therebetween to carry out the functions of control system 112. No particular spatial arrangement of such components is required. The components of control system 112 may be located away from other components of monitoring system 100, or one or more of these components may be located near or configured as part of other components of monitoring system 100.

As stated above, sensor 106 is preferably configured to measure a first sample attribute value for the first sample attribute and second sample attribute value for the second sample attribute at times in which the first sample flow and second sample flow are each transported through sensor 106. Control system 112 is preferably configured to receive a first sample attribute value and a second sample attribute value measured by the sensor from the sensor. Communication between control system 112 and sensor 106 may be carried out over a serial interface such as RS-232C. Control system 112 preferably includes a display unit configured to display the first sample attribute value and the second sample attribute value. Control system 112 is preferably configured to display only filtered measurements from sensor 106. Preferably, control system 112 may be configured to exclude the first numJunk measured sample attribute values transmitted by sensor 106, and to then average the next numMeas measured sample attribute values transmitted by sensor 106 to produce a filtered sample attribute value. The filtered sample attribute value may then be displayed by the display unit. Such filtering preferably ensures that the measurements displayed by control system 112 are "good" measurements. Control system 112 may be further configured, however, to transmit raw, unfiltered measured sample attribute values to another source for logging.

A monitoring system as described herein may further be configured to detect when an attribute has departed from a desired attribute value range and to provide appropriate notification thereof. In an embodiment, control system 112 is configured to determine whether the first sample attribute value is outside of a first sample attribute value range bounded by a low first sample attribute value and a high first sample attribute value. The high and low sample attribute values may represent minimum and maximum preferred values of the first sample attribute. Upon detection that the first sample attribute values is outside of the first sample attribute value range, the control system is preferably configured to generate an out-of-tolerance signal for the first sample flow. Control system 112 may be similarly configured for a second sample flow of the second chemical mixture, as well as for other sample flows from other chemical mixtures. The control system's ability to determine whether a measured sample attribute value is out-of-tolerance may be based only on its own ability to analyze measured values received from the sensor, or may consist of the control system receiving a signal from the sensor relating whether a measured value is within one or more attribute value ranges.

In an embodiment, the first sample attribute value range is a primary first sample attribute value range, and the low and high first sample attribute values are primary low and high first sample attribute values. Control system 112 may then be configured to determine whether a first sample attribute value is outside of a secondary first sample attribute value range bounded by a secondary low first sample attribute value and a secondary high first sample attribute value. The secondary first sample attribute value range is preferably greater than the primary first sample attribute value range. Upon determination that the first sample attribute value is outside the secondary first sample attribute value range, control system 112 is preferably configured to transmit an inhibit signal to a processing tool configured to use the first chemical mixture in processing. The processing tool (not shown) is preferably configured to refrain from using the first chemical mixture in processing upon receipt thereof. As was the case above, the control system's ability to determine whether a measured sample attribute value is outside of a secondary sample attribute value range may be based on its own ability to perform such a determination, or on its receiving notification from, e.g., the sensor that the measured sample attribute value is outside of the secondary sample attribute value range.

Control system 112 is preferably also configured to direct the operation of supply distribution system 108 and return distribution system 110. By transmitting appropriate signals to components of the supply and return distribution systems, control system 112 is preferably capable of selecting which flows are to be transported to and from sensor 106. For example, control system 112 may direct the transporting of a first sample flow of the first chemical mixture from first chemical vessel 102 by directing the operation of valves within supply distribution system 108 to create a fluid flow path between first chemical vessel 102 and sensor 106.

Control system 112 may then direct the operation of a pump within supply distribution system 108 to transport the first sample flow to sensor 106. Subsequently, control system 112 may direct the operation of valves within return distribution system 110 to transport the first sample flow to drain 118 or back to first chemical vessel 102.

The actions of the monitoring system are preferably at least partially directed through software. The software instructions may be at least temporarily stored in a storage element of the storage system, such as storage element 114. The storage element may be any type of media configured to store, if only temporarily, several groupings of instructions for carrying out several processing steps. Possibilities for storage element 114 include, but are not limited to, magnetic media (e.g., hard drives and floppy disks) and semiconductor memory (e.g., RAM and ROM). Storage element 114 may be located within an element of control system 112 such as a programmable controller, or may be configured as part of a device distally located from other components of control system 112.

Figure 3:
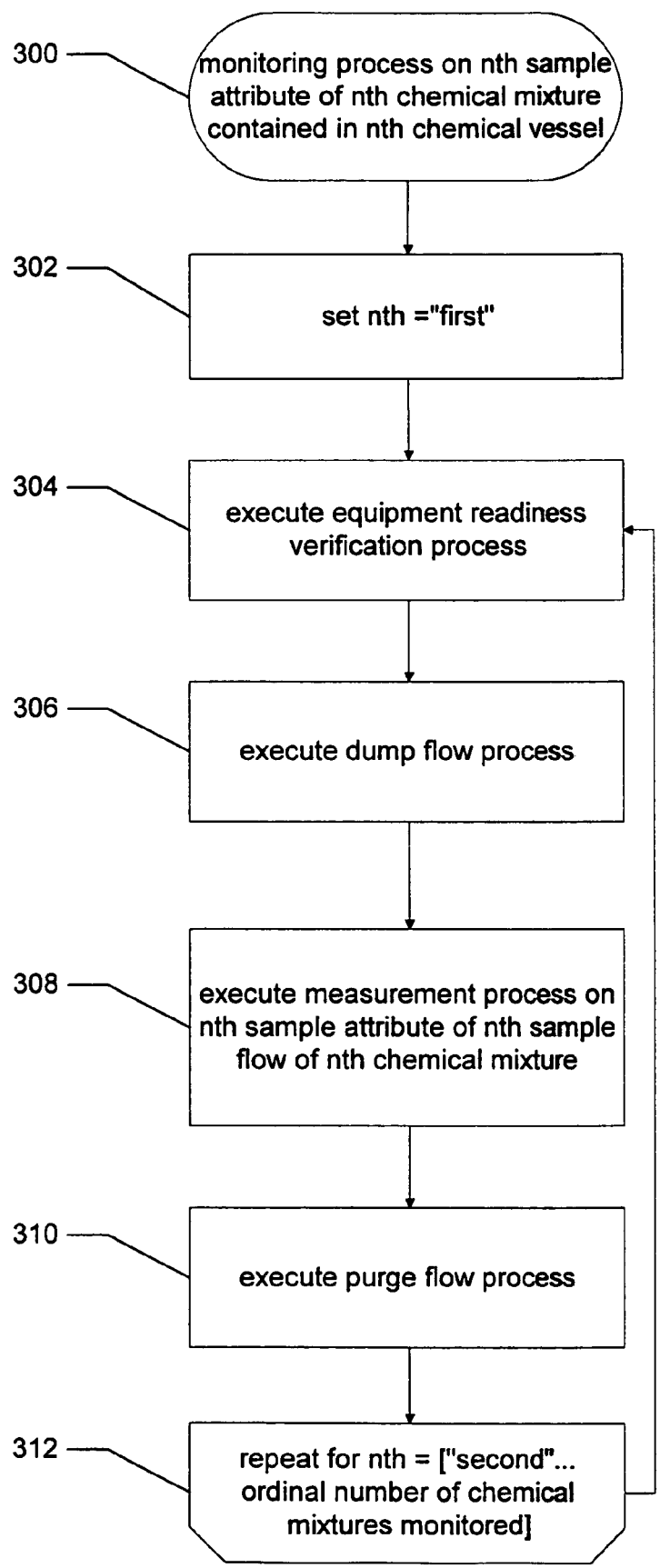
FIG. 3 is a flow diagram of a monitoring process for monitoring an nth sample attribute of an nth chemical mixture.

Processing steps by which programming instructions, preferably residing in storage element 114, can direct the operation of monitoring system 100 are shown in FIGS. 3–9. As shown in FIG. 3, the processing steps preferably include a monitoring process 300. Monitoring process 300 is preferably configured to monitor an nth sample attribute of an nth chemical mixture contained in an nth chemical vessel. Monitoring process 300 preferably initiates monitoring on the first chemical mixture by setting nth equal to "first" (step 302) so that monitoring process 300 will be carried out on the first chemical mixture. Monitoring process 300 then preferably executes processing step 304, an equipment readiness verification process. Subsequently, a dump flow process may be executed as processing step 306. A measurement process may then be executed as processing step 308. The measurement process 308 is preferably executed for the nth sample attribute of the nth sample flow of the nth chemical mixture. Subsequently, purge flow process 310 may be executed. Processing steps 304, 306, 308, and 310 may be repeated for nth=["second" . . . the ordinal number of chemical mixtures monitored] (step 312). That is, the processing steps of monitoring process 300 may be repeated for a second chemical mixture, a third chemical mixture, a fourth chemical mixture, etc., until the process has been repeated for all chemical mixtures being monitored by monitoring system 100 (however, it is not required to repeat the steps in any particular order). Additionally, a termination signal may be sent to control system 112 at any point within monitoring process 300 to terminate execution of the process.

The above-described processing steps, which are executable by control system 112, preferably direct the performance of respective operational sequences within monitoring system 100. For example, executing monitoring process 300 preferably results in the performance of a monitoring sequence on an nth sample attribute of an nth sample flow of the nth chemical mixture. The monitoring sequence preferably includes performing an equipment readiness verification sequence upon execution of equipment readiness verification process 304, performing a dump flow sequence upon execution of dump flow process 306, performing a measurement sequence upon execution of measurement process 308, and performing a purge flow sequence upon execution of purge flow process 310. Control system 112 is preferably configured to direct the repetition of the above-described sequences as directed by the programming instructions.

Figure 4:
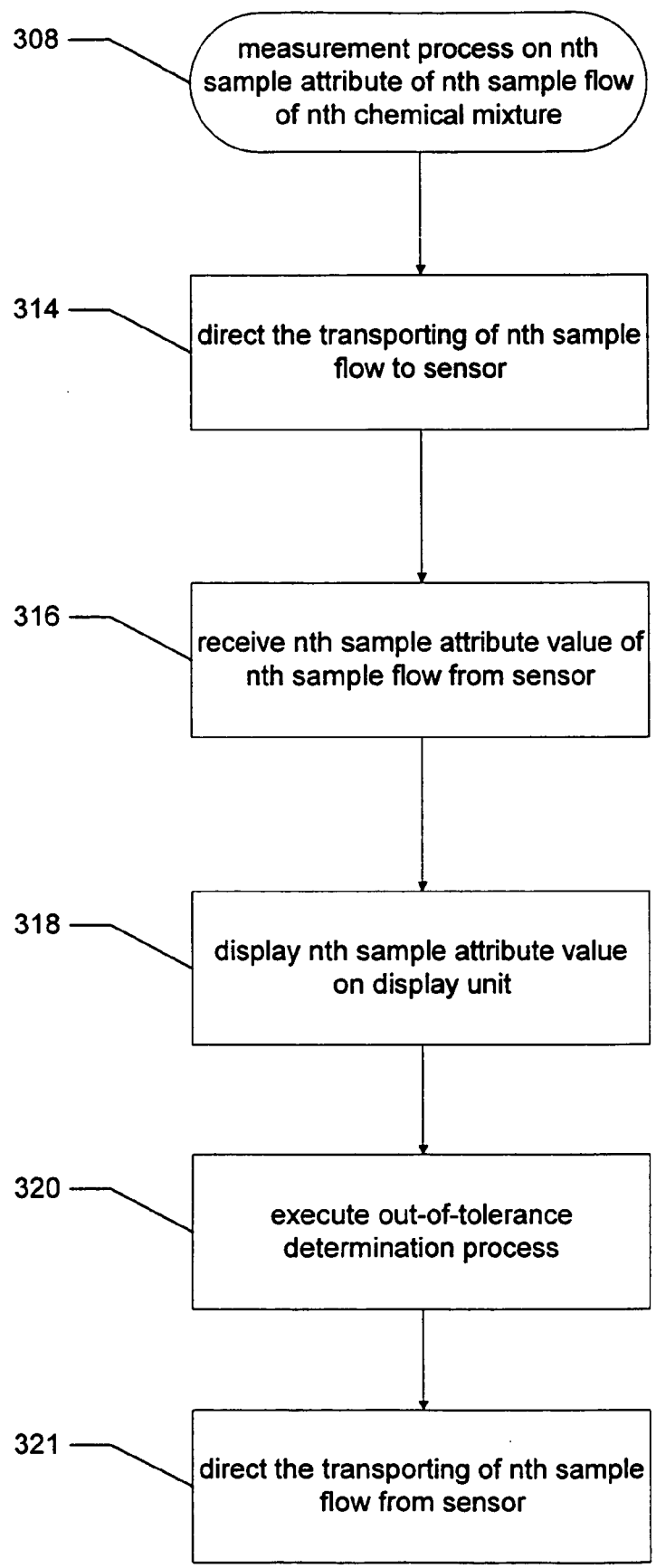
FIG. 4 is a flow diagram of a measurement process executable in the monitoring process shown in FIG. 3.

FIG. 4 shows processing steps that may be executed as part of measurement process 308. Execution of processing step 314 by control system 212 preferably directs the transporting of an nth sample flow to sensor 106. Execution of processing step 314 preferably results in control system 112 transmitting one or more appropriate signals to supply distribution system 108 to direct the transporting of the nth sample flow to sensor 106. Such signals may include direction to open the nth supply valve and other valves within a supply manifold of supply distribution system 108 for placing sensor 106 in fluid communication with the nth chemical vessel (e.g., first chemical vessel 102 or second chemical vessel 104). Execution of processing step 314 may preferably further include directing supply distribution system 108 to activate a pump for transporting the nth sample flow to sensor 106. The transporting of the nth sample flow to sensor 106 may be directed to be performed at a substantially constant flow rate.

As the nth sample flow is transported through sensor 106, sensor 106 may measure an nth sample attribute of the nth sample flow to produce an nth sample attribute value. If sensor 106 is a concentration sensor, sensor 106 may measure an nth concentration of a first chemical (e.g., a hydrogen peroxide concentration) within the nth sample flow. Whatever the sample attribute measured by sensor 106, that sample attribute is preferably transmitted to the control system after measurement. Control system 112 may then be directed to receive the nth sample attribute value from sensor 106 (step 316). An out-of-tolerance determination process 320 may then be executed for each nth sample attribute value measured. Processing step 321 may then be executed to direct the transport of the nth sample flow from sensor 106. Execution of processing step 321 preferably results in control system 112 transmitting an appropriate signal to return distribution system 110 to direct the system to transport the nth sample flow from sensor 106. Such a signal may include direction to open and close various valves within return distribution system 110 for placing sensor 106 in fluid communication with the nth chemical vessel (e.g., first chemical vessel 102 or second chemical vessel 104) to allow the nth sample flow to be recycled. Alternately, the signal may include direction to open and close various valves within return distribution system 110 for placing sensor 106 in fluid communication with drain 118 for disposal of the nth sample flow.

Figure 5:
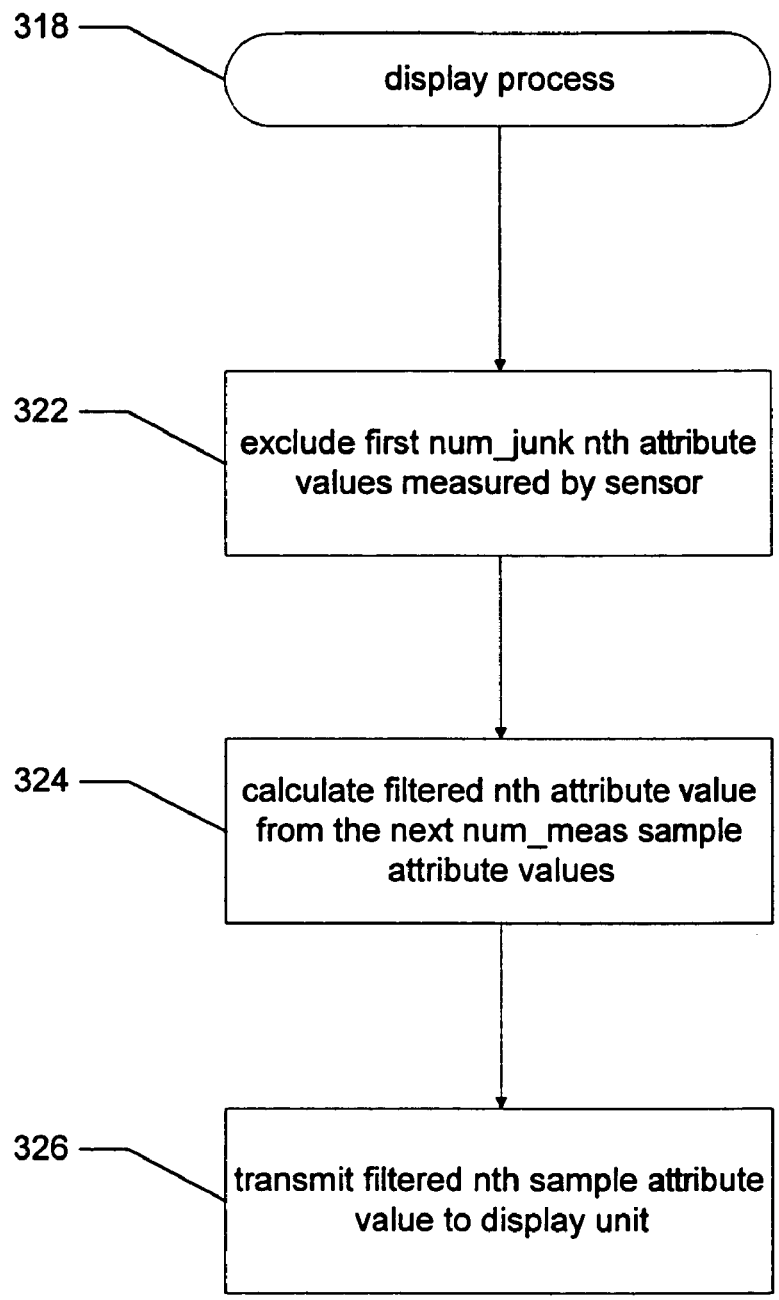
FIG. 5 is a flow diagram of a display process executable in the measurement process shown in FIG. 4.

FIG. 5 shows processing steps that may be executed as part of display process 318. In processing step 322, the first numJunk values measured by sensor 106 are excluded, or dropped. Dropping an initial set of measurements transmitted by sensor 106 may help ensure that the sample attribute values used in calculating a filtered sample attribute value are the most accurate, and may also help synchronize signal transmission between sensor 106 and control system 112. In an embodiment, numJunk is set to three measurements. The filtered nth sample attribute value may then be calculated from the next numMeas nth sample attribute values. In an embodiment, numMeas is set to two measurements. The filtered nth sample attribute value may then be transmitted to a display unit for display (step 326).

Figure 6:
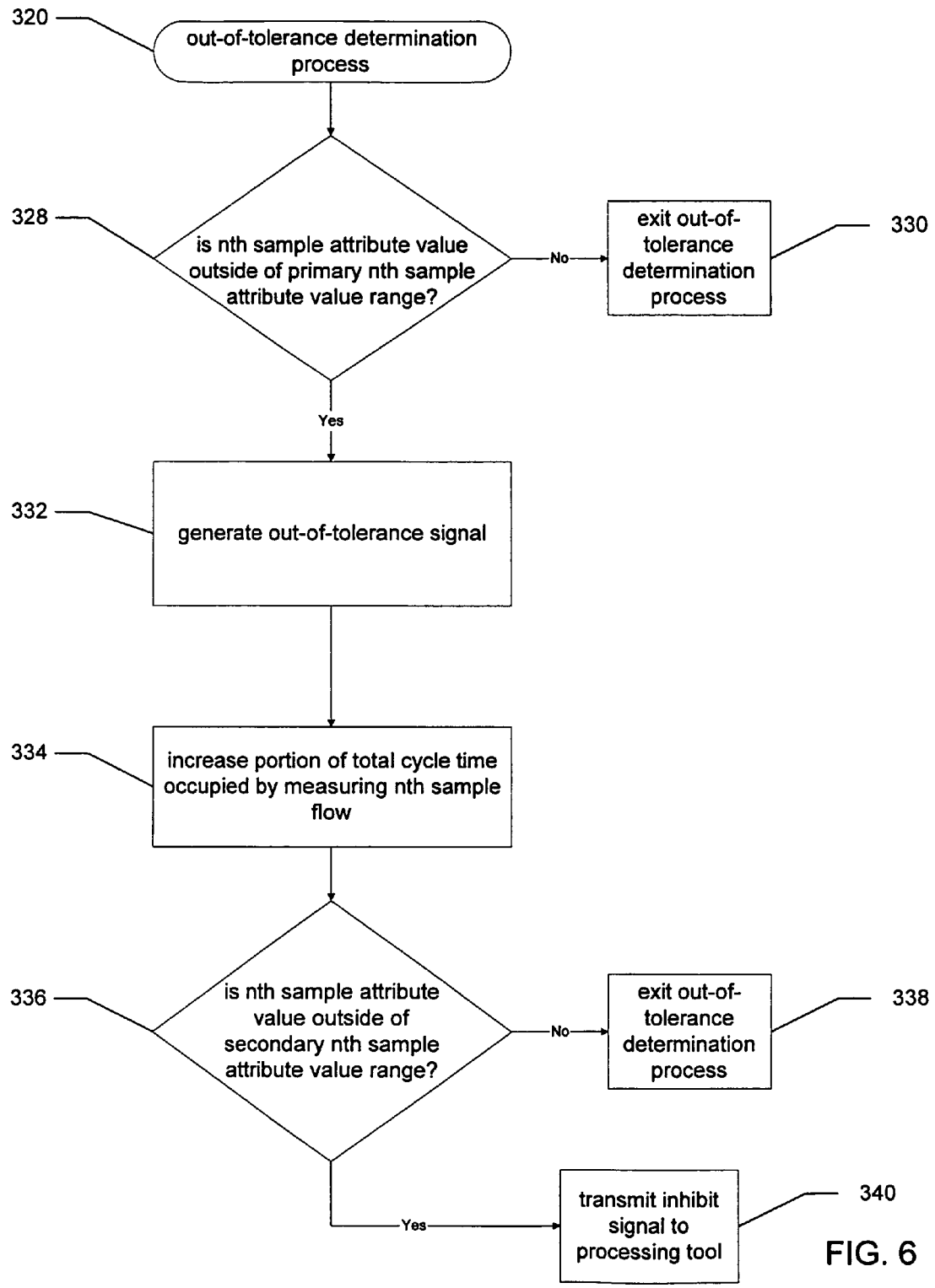
FIG. 6 is a flow diagram of an out-of-tolerance determination process executable in the measurement process shown in FIG. 4.

FIG. 6 shows processing steps that may be executed as part of out-of-tolerance determination process 320. Processing step 328 preferably determines whether an nth sample attribute value measured by sensor 106 is outside of a primary nth sample attribute value range bounded by a primary low nth sample attribute value and a primary high nth sample attribute value. If the nth sample attribute value is within the primary nth sample attribute value range, out-of-tolerance determination process 320 is preferably exited (processing step 330). If the nth sample attribute value is outside the primary nth sample attribute value range, an out-of-tolerance signal is preferably generated by control system 112 (processing step 332). The out-of tolerance signal may be displayed by a display unit to, e.g., warn operators that the nth sample attribute value is outside of a desirable range.

A length of time between instances of repeating monitoring process 300 for a particular nth chemical mixture may be considered a total cycle time (e.g., the total length of time involved in executing monitoring process 300 once for all chemical mixtures being monitored). In addition to generating an out-of-tolerance signal, processing step 320 may further include increasing the portion of a total cycle time occupied by measuring the nth sample flow (processing step 334). Such increasing may include lengthening the duration for which measurement process 308 is executed, possibly to the extent that the nth sample flow is the only sample flow monitored until the out-of-tolerance condition is resolved. Processing step 334 is optional, however.

Out-of-tolerance determination process 320 preferably also includes processing step 336 for determining whether the nth sample attribute value is outside of a secondary nth sample attribute range bounded by a secondary low nth sample attribute value and a secondary high nth sample attribute value. The secondary nth sample attribute value range is preferably greater than the primary nth sample attribute value range. Upon determining that the nth sample attribute value is outside the secondary nth sample attribute value range, control system 112 preferably generates and transmits an inhibit signal (e.g., a "start inhibit" or "no-go" signal) to a processing tool configured to use the first chemical mixture in processing (processing step 340). The processing tool is preferably configured to refrain from using the first chemical mixture in processing upon receipt thereof. If the nth sample attribute value is within a secondary nth sample attribute value range, out-of-tolerance determination process 320 is preferably exited (processing step 338). After exiting out-of-tolerance determination process 320, monitoring process 300 preferably resumes with purge flow process 310.

Figure 7:
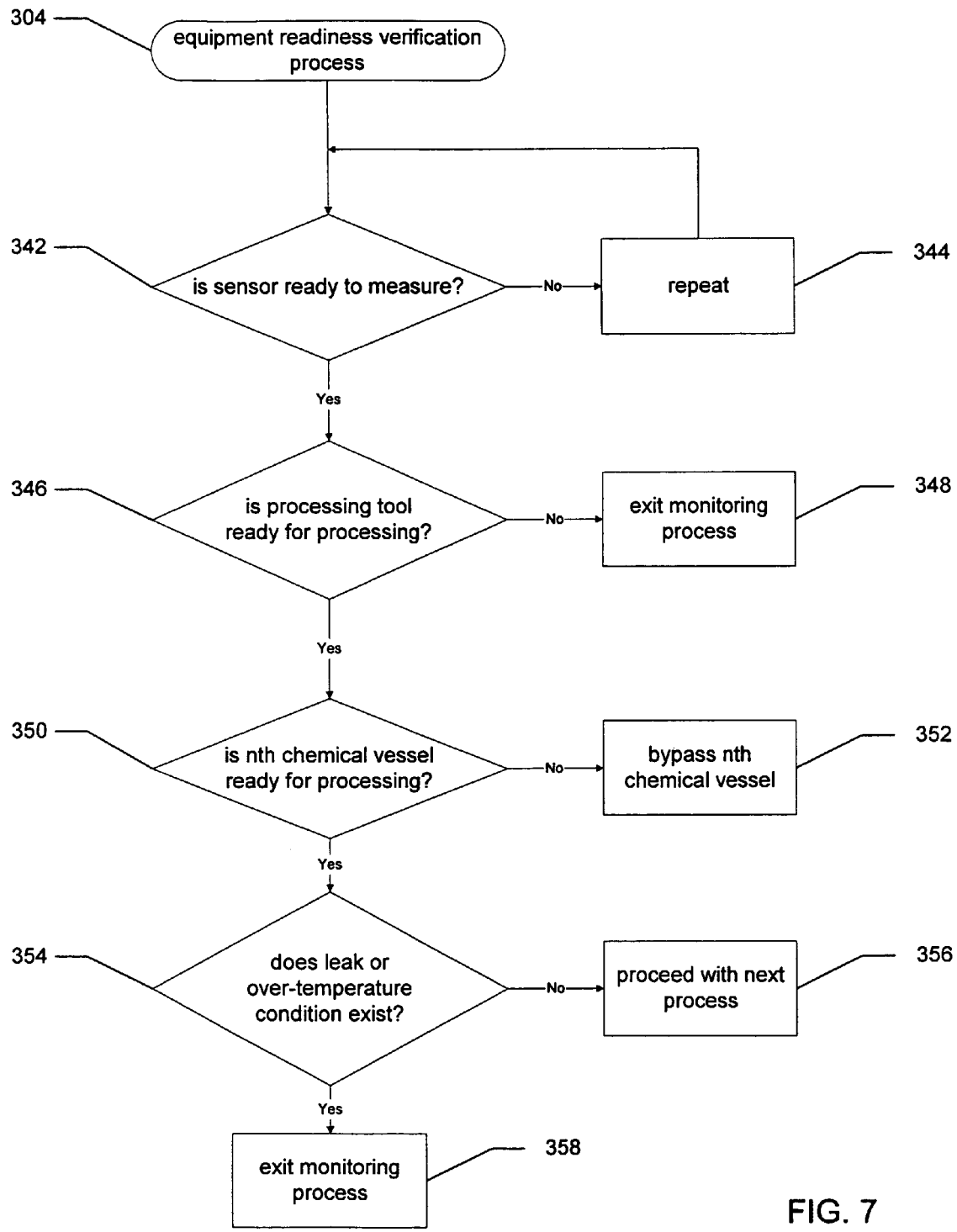
FIG. 7 is a flow diagram of an equipment readiness verification process executable in the monitoring process shown in FIG. 3.

FIG. 7 shows processing steps that may be performed as part of equipment readiness verification process 304. In processing step 342, it may be determined whether sensor 106 is ready to measure (i.e., ready to begin taking and transmitting measured sample attribute values). Sensor 106 may not be ready to measure because, e.g., it is warming up. If sensor 106 is not ready to measure, the processing step 342 is preferably repeated after a predetermined length of time (processing step 344). If sensor 106 is ready to measure, it may then be determined whether a processing tool configured to use the nth chemical mixture in processing is ready for processing (processing step 346). If the processing tool not ready for processing, monitoring process 300 is preferably exited to resolve the problem (processing step 348). If the processing tool is ready for processing, it may then be determined whether the nth chemical vessel is ready for processing. The nth chemical vessel may not be ready for processing because, e.g., it is set up as a spare chemical vessel or it is undergoing a maintenance process. In such a case, the execution of monitoring process 300 may be bypassed for the nth chemical vessel (processing step 352), and monitoring process 300 may begin anew with another chemical vessel.

If the nth chemical vessel is ready for processing, it may then be determined whether a leak or over-temperature condition exists within the processing tool, or in other components of monitoring system 100 (processing step 354). If such a condition is detected, monitoring process 300 is preferably exited to resolve the problem (processing step 358). Otherwise, monitoring process 300 may proceed with the next process (processing step 356), which is preferably dump flow process 306.

Figure 8:
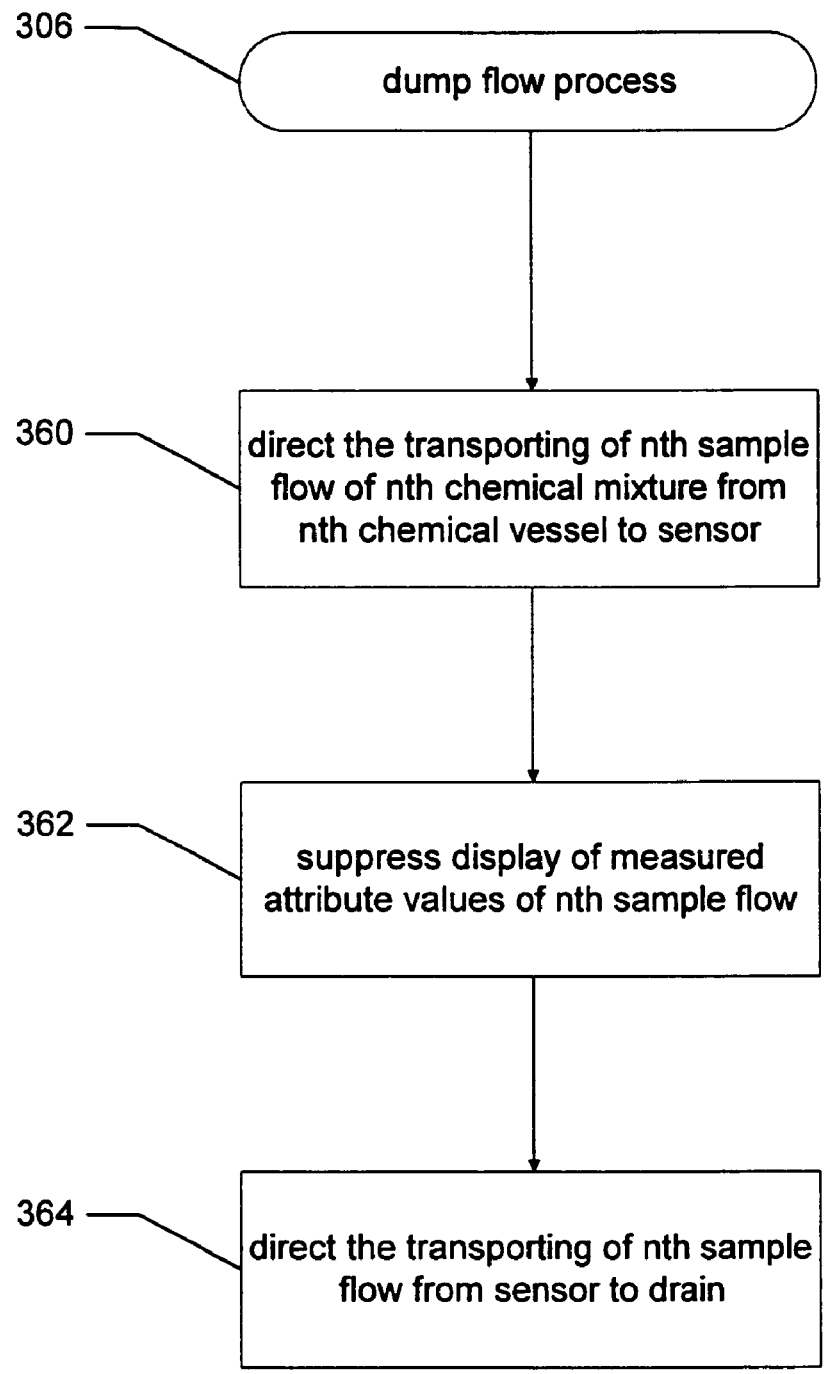
FIG. 8 is a flow diagram of a dump flow process executable in the monitoring process shown in FIG. 3.

FIG. 8 shows processing steps that may be performed as part of dump flow process 306. Dump flow process 306 is preferably executed prior to measurement process 308. As stated above, an nth sample flow transported to sensor 106 during measurement process 308 is preferably returned to the nth chemical vessel that it originated from. A goal of the dump flow sequence initiated by the execution of dump flow process 306 is to help ensure that any materials remaining from previous measurement sequences are substantially cleared out of fluid flow paths of monitoring system 100 before a new sample flow is transported through the monitoring system. Dump flow process 306 may also serve to acclimate sensor 106 to a sample flow, potentially allowing more accurate measurements to be obtained.

In dump flow process 306, processing step 360 is preferably executed to direct the transporting of an nth sample flow of the nth chemical mixture from the nth chemical vessel to sensor 106. The process of transporting the nth sample flow to sensor 106 in dump flow process 306 is preferably similar to the process of transporting the nth sample flow to sensor 106 in measurement process 308. During dump flow process 306, however, the display of measured attribute values of the nth sample flow is preferably suppressed (processing step 362). Such suppression may involve, e.g., sensor 106 not taking sample attribute value measurements during dump flow process 306 or control system 112 ignoring measurement values transmitted by the sensor during the purge flow process. Processing step 364 may then be executed to direct the transporting of the nth sample flow from sensor 106 to drain 118.

Figure 9:
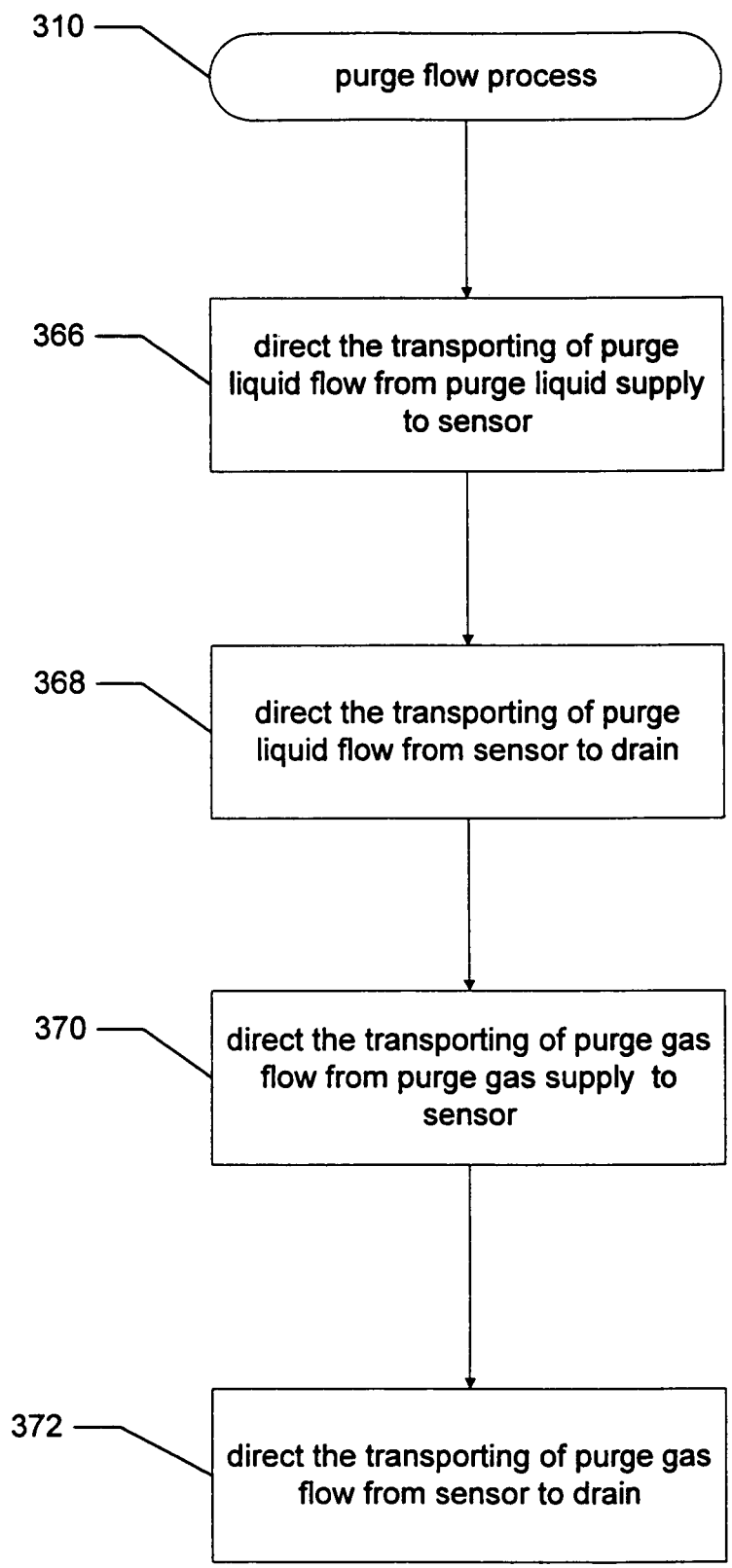
FIG. 9 is a flow diagram of a purge flow process executable in the monitoring process shown in FIG. 3.

FIG. 9 shows processing steps that may be performed as part of purge flow process 310. A purge flow process 310 may be performed to remove chemicals remaining after transporting a sample flow through monitoring system 100. In purge flow process 310, purge fluids are preferably transported from purge fluid supply 116 to sensor 106 through supply distribution system 108. As stated above, purge fluid supply 116 may include a purge liquid supply and a purge gas supply. The purge liquid supply is preferably deionized water, and the purge gas supply is preferably nitrogen gas. Processing step 366 may be executed to direct the transporting of a purge liquid flow from the purge liquid supply to sensor 106. The purge liquid flow may be subsequently transported from sensor 106 to drain 118 (processing step 368). Processing step 370 may be executed to direct the transporting of a purge gas flow from the purge gas supply to sensor 106. Subsequently, processing step 370 may be executed to direct the transporting of the purge gas flow from sensor 106 to drain 118.

As may be seen from the above, dump flow process 306 and purge flow process 310 may both be configured to reduce the amount of contamination remaining from a previous measurement sequence and thus lessen the incidence of cross-talk between the measurements of different sample flows. In addition, both processes may assist in reducing the chance that chemicals remaining from one sample flow will be transported to a different chemical vessel than that from which they originated. In light of the above, it may not be necessary to use both a dump flow sequence and a purge flow sequence, or either. Also, the various durations of these processes may be extended or shortened in view of the particular goals of a monitoring process. The total amount time necessary for purge flow and dump flow processes may be largely dependent on factors such as the sensitivity of the sensor used and the similarity of compositions of the chemical mixtures being monitored. If the chemical mixtures monitored by the monitoring system are similar, it may be unnecessary for the purge flow and/or dump flow processes to be extended to a point where all residue remaining from a sample flow is substantially removed. Alternately, it may be helpful to extend the length of in the purge flow and/or dump flow processes when the compositions of the chemical mixtures being monitored vary substantially.

It should be understood that the constituent processing steps of monitoring process 300 are not required to be performed in the order shown in the Drawings. In addition, some processes may not be performed on each loop through the chemical mixtures. For example, it may only be necessary to determine whether sensor 106 is ready to measure once per execution of monitoring process 300. And, of course, some processing steps may not be performed at all. In addition, monitoring process 300 may be manually exited at any time.

Figure 2:
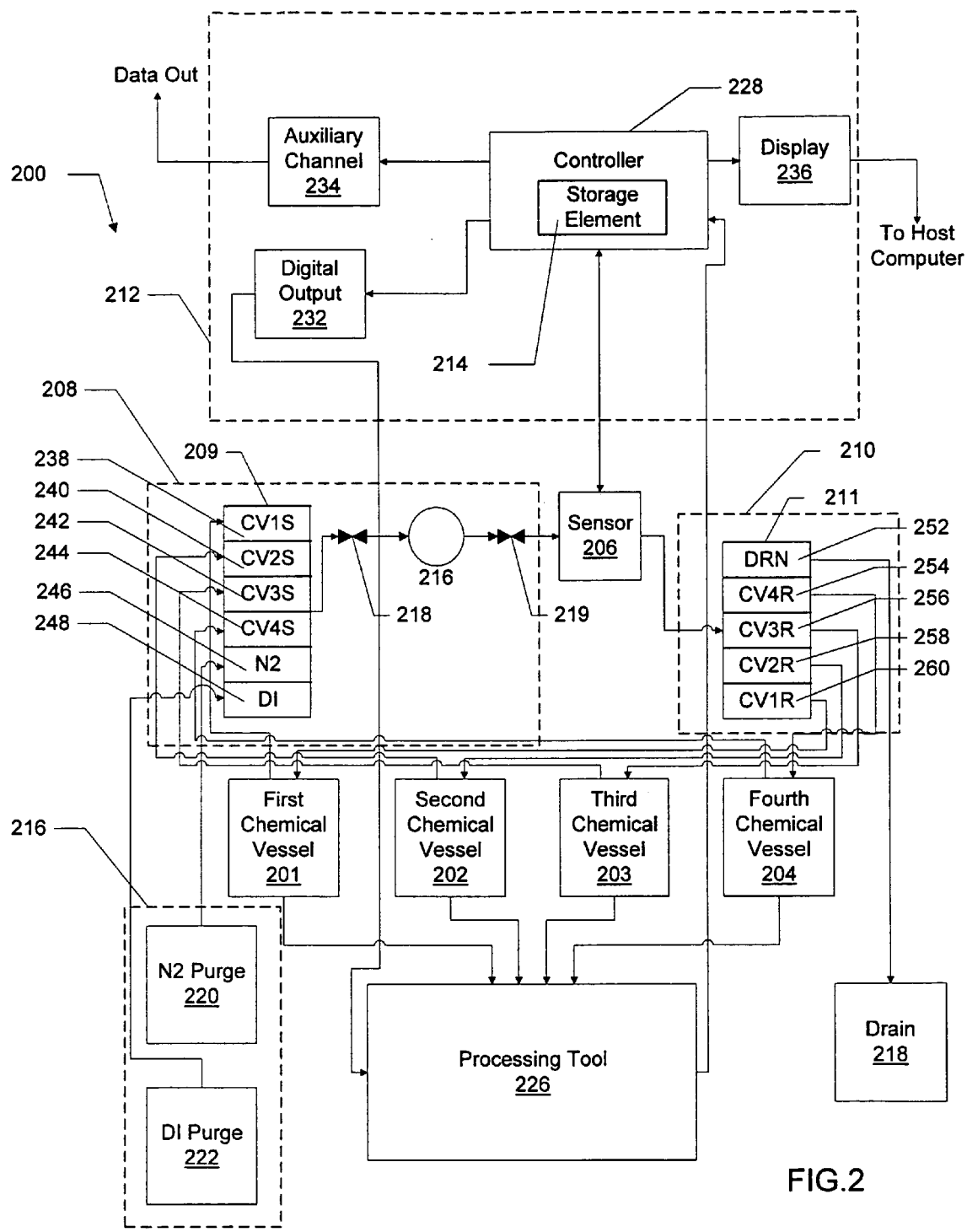
FIG. 2 is a schematic view of a further embodiment of a monitoring system.

FIG. 2 presents monitoring system 200. Monitoring system 200 may be configured to perform some or all of the functions monitoring system 100 may be configured to perform. Monitoring system 200 is preferably configured to monitor one or more attributes of multiple chemical mixtures contained in multiple chemical vessels. In the embodiment shown in FIG. 2, monitoring system 200 includes a first chemical vessel 201, a second chemical vessel 202, a third chemical vessel 203, and a fourth chemical vessel 204. First chemical vessel 201 preferably contains a first chemical mixture. Likewise, second, third, and fourth chemical vessels 202, 203, and 204 preferably contain second, third, and fourth chemical mixtures, respectively. In addition, monitoring system 200 preferably includes sensor 206. Sensor 206 is preferably configured to selectively receive a first sample flow of the first chemical mixture from the first chemical vessel, a second sample flow of the second chemical mixture from the second chemical vessel, a third sample flow of the third chemical mixture from the third chemical vessel, and a fourth sample flow of the fourth chemical mixture from the fourth chemical vessel. Preferably, sensor 206 is configured to measure a first sample attribute of the first sample flow, a second sample attribute of the second sample flow, a third sample attribute of the third sample flow, and a fourth sample attribute of the fourth sample flow. By multiplexing multiple sample flows through sensor 206, monitoring system 200 may monitor an attribute of multiple chemical mixtures without having to use separate sensors for each chemical monitored.

First chemical vessel 201, second chemical vessel 202, third chemical vessel 203, and fourth chemical vessel 204 may be similarly configured to first and second chemical vessels 102 and 104. First chemical vessel 201, second chemical vessel 202, third chemical vessel 203, and fourth chemical vessel 204 may be used to store chemical mixtures for use by processing tool 226.

The first, second, third, and fourth chemical mixtures within the first, second, third, and fourth chemical vessels 201, 202, 203, and 204, respectively, may be any of the variety capable of having an attribute measured by a sensor, and may be configured similarly to the first and second chemical mixtures described in respect to FIG. 1. When at desired levels, the first, second, third, and fourth chemical mixtures are preferably substantially the same mixture (i.e., they have substantially the same chemicals at substantially the same concentrations). Preferably, the first, second, third, and fourth chemical mixtures each contain at least a first chemical and a second chemical. In an embodiment, the first, second, third, and fourth chemical mixtures are liquid chemical mixtures, and preferably SC1 solutions. In such a case, the first and second chemicals may be considered to be any one of hydrogen peroxide, ammonium hydroxide, or water.

Processing tool 226 may be a machine, apparatus, or the like configured for use in chemical processing. Preferably, processing tool 226 is configured for use in semiconductor fabrication processes. Processing tool 226 preferably is configured to use the first, second, third, and fourth chemical mixtures to process semiconductor substrates (e.g., single-crystal silicon wafers) and any materials formed thereupon. Preferably, processing tool 226 is a multi-chamber tool, and each chamber of the tool may be configured to be supplied by one or more of the first, second, third, and fourth chemical mixtures. Monitoring system 200 may be configured such that the number of chemical vessels containing chemical mixtures is greater than the number of processing chambers within processing tool 226. In such a case, one or more of the chemical vessels may be used as a spare chemical vessel. In an embodiment, second chemical vessel 202 is set up as a spare chemical vessel. During operation, processing tool 226 may be capable of transporting the first, second, third, or fourth chemical mixtures from the first, second, third, or fourth chemical vessels, respectively, to be used, e.g., to clean one or more wafers after the wafers have undergone another processing step (e.g., a CMP processing step or a metal etch step). In an embodiment, processing tool 226 is a spray-cleaning process tool, and preferably is a Semitool Spray Acid Tool, commercially available from Semitool, Inc., Kalispell, Mont.

Sensor 206 may be part of a larger sampling subsystem including all components of monitoring system 200 configured to selectively transport fluid flow to sensor 206, measure one or more fluid flow attributes (if desired), and transport fluid flow away from the sensor (components of the sampling subsystem may also be configured to perform numerous functions other than and outside of the scope of those mentioned above). As part of the sampling subsystem, monitoring system 200 preferably includes supply distribution system 208. Supply distribution system 208 may be configured to perform some or all of the functions that supply distribution system 108 may be configured to perform. As shown in FIG. 2, supply distribution system 208 preferably includes supply manifold 209. Supply manifold 209 is preferably configured to selectively place sensor 206 in fluid communication with a chemical vessel by selective actuation of its constituent valves. Supply manifold 209 may be connected to the first, second, third, and fourth chemical vessels through piping. Supply manifold 209 preferably includes at least one supply valve for each chemical vessel attached thereto.

Each supply valve is preferably configured to prevent or permit fluid flow from a respective chemical vessel to sensor 206. Opening of a supply valve preferably places a respective chemical vessel in fluid communication with supply manifold 209. As such, a supply valve is preferably only opened if all other supply valves are closed. As shown in FIG. 2, supply manifold 209 preferably includes first supply valve 238 (CV1S), second supply valve 240 (CV2S), third supply valve 242 (CV3S), and fourth supply valve 244 (CV4S). Each supply valve may be implemented as a single valve or as a series of valves within supply manifold 209. Supply valves 238, 240, 242, and 244 may be solenoid valves, configured to be actuated upon receipt of an appropriate signal.

Supply distribution system 208 preferably also includes pump 216, which may be arranged downstream of supply manifold 209. Pump 216 is preferably configured to pump fluid flow to sensor 216. In an embodiment, pump 216 is a positive displacement pump. Preferably, pump 216 is configured to transport fluid flow to sensor 206 at a substantially constant flow rate. Check valves 218 and 219 may be respectively arranged upstream and downstream of pump 216. Check vales 218 and 219 preferably are configured to prevent fluid backflow.

After sensor 206 has been placed in fluid communication with a particular chemical vessel, pump 216 may be configured to transport a sample flow of the chemical mixture contained in the chemical vessel. In such a manner, a first sample flow of the first chemical mixture may be transported from first chemical vessel 202 to sensor 206, a second sample flow of the second chemical mixture may be transported from second chemical vessel 202 to sensor 206, a third sample flow of the third chemical mixture may be transported from third chemical vessel 203 to sensor 206, and a fourth sample flow of the fourth chemical mixture may be transported from fourth chemical vessel 204 to sensor 206.

Monitoring system 200 may further include return distribution system 210. Return distribution system 210 may be configured to perform some or all of the functions that return distribution system 110 may be configured to perform. As shown in FIG. 2, return distribution system 210 may further include a return manifold 211. Return manifold 211 is preferably arranged downstream of sensor 206, and may be connected to sensor 206 by a return flow line. Return manifold 211 may be connected to the first, second, third, and fourth chemical vessels through piping. Preferably, return manifold 211 may be configured to selectively place sensor 206 in fluid communication with a chemical vessel by selective actuation of its constituent return valves. Return manifold 211 preferably includes at least one return valve for each chemical vessel attached thereto. Each return valve is preferably configured to prevent or permit fluid flow from sensor 206 to a respective chemical vessel. Opening of a return valve preferably places a respective chemical vessel in fluid communication with return manifold 211. As such, a return valve is preferably only opened if all other return valves are closed.

As shown in FIG. 2, return manifold 211 preferably includes first return valve 254 (CV1R), second return valve 256 (CV2R), third return valve 258 (CV3R), and fourth return valve 260 (CV4R). Each return valve may be implemented as a single valve or as a series of valves within return manifold 211. Return valves 254, 256, 258, and 260 may be solenoid valves, configured to be actuated upon receipt of an appropriate signal. During operation, return manifold 209 may be configured to selectively return a first sample flow to first chemical vessel 202, a second sample flow to second chemical vessel 202, a third sample flow to third chemical vessel 203, and a fourth sample flow to fourth chemical vessel 204.

Monitoring system 200 preferably also includes a purge fluid supply 216. Purge fluid supply 216 may be configured to perform one or more of the functions of purge fluid supply 116. Purge fluid supply 216 preferably includes N2 purge supply 220 and DI purge supply 222. Supply manifold 209 may be configured to be in selective fluid communication with N2 purge supply 220 and DI purge supply 222. To this end, supply manifold 209 preferably includes a N2 purge valve 246 and a DI purge valve 248. N2 purge valve 246 is preferably configured to prevent or permit the flow of nitrogen gas from N2 purge supply 220 to sensor 206. When N2 purge valve 246 is opened, nitrogen gas may be transported to sensor 206, preferably as part of a purge process. DI purge valve 248 is preferably configured to prevent or permit the flow of deionized water from N2 purge supply to sensor 206. When DI purge valve 248 is opened, deionized water may be transported to sensor 206, preferably as part of a purge process. N2 purge valve 246 and a DI purge valve 248 are preferably solenoid valves.

Monitoring system 200 preferably also includes drain 218. Drain 218 is preferably configured similarly to drain 118. Return manifold 211 is preferably configured to selectively place sensor 206 is fluid communication with drain 218 such that fluids leaving sensor 206 may be transported to drain 218. Return manifold 211 may include a drain valve 252 configured to prevent or permit fluid flow from sensor 206 to drain 218. Drain valve 252 is preferably a solenoid valve.

Sensor 206 may be configured to perform one or more of the functions that sensor 106 may be configured to perform. In a preferred embodiment, sensor 206 is configured to measure chemical concentrations within a sample flow transported through the sensor. Sensor 206 is preferably configured to measure a first sample concentration of a first chemical and a second sample concentration of a second chemical within a sample flow being transported through the sensor. As stated above, the first and second chemicals may be any of the constituent chemicals of a chemical mixture. In an embodiment where the first, second, third, and fourth chemical mixtures are SC1 solutions, the first and second chemicals may each be water, hydrogen peroxide, or ammonium hydroxide. Sensor 206 is preferably configured to transmit a signal representing a measured concentration value of a sample flow to another device (e.g., a control system).

Sensor 206 is further preferably configured to measure a plurality of sample attributes of a sample flow. In addition to being configured to measure concentrations of chemical components of a sample flow, sensor 206 may be configured to measure attributes such as temperature or resistivity. In an embodiment in which first and second chemical mixtures are configured as SC1 solutions, the sensor is preferably configured to measure the solution temperature as well as the respective concentrations of ammonia hydroxide, hydrogen peroxide, water, and any other chemicals present. The ability to monitor multiple attributes of a sample flow may allow for a more accurate reading of one or more of the attributes measured to be reported. For example, the ability to measure solution temperature may allow more accurate concentrations of the sample flow chemical components to be reported by sensor 206 or to be calculated by other components of monitoring system 200.

Monitoring system 200 also preferably includes control system 212. Control system 212 is preferably configured to perform one or more of the functions of control system 112. Control system 212 is preferably configured to interface with the various components of monitoring system 200 to direct a monitoring process. Control system 212 preferably includes controller 228. Controller 228 is preferably a programmable controller. A suitable programmable controller is the Z-World PK2200, commercially available from Z-World, Davis, Calif. Controller 228 preferably has multiple digital inputs and multiple digital outputs. Preferably, controller 228 also includes at least one serial interface port. Controller 228 may communicate with other devices through its input and output ports. Controller 228 may include an enclosure for protection from, e.g., chemical attack.

Controller 228 is preferably configured to receive measured sample attribute values from sensor 206. Preferably, controller 228 is configured to achieve measured concentrations of sample flows transported through sensor 206. Communication between controller 228 and sensor 206 is preferably carried out over a serial interface, such as RS-232C.

Control system 212 also preferably includes display unit 236. Display unit 236 is preferably configured to display sample attribute values transmitted from controller 228. In an embodiment, display unit 236 may be capable of transmitting data received from control 228 away from monitoring system 200 (e.g., to a host computer and/or Factory Automation). Controller 228 is preferably configured to communicate with display unit 236 over a serial interface, such as RS-485. Display unit 236 may be a display unit such as the Z-World OP7100.

Preferably, controller 228 is configured to transmit filtered sample attribute values to display unit 236. For example, controller 228 may be configured to exclude the first numJunk measured sample concentration values transmitted by sensor 206, and to then average the next numMeas measured sample concentration values transmitted by sensor 206 to produce a filtered sample concentration value. The filtered sample concentration value may then be displayed by the display unit. Such filtering preferably ensures that the measurements displayed by control system 212 are "good" measurements (i.e., they are representative of conditions within the respective chemical mixture).

Control system 212 may be further configured, however, to transmit raw, unfiltered measured sample attribute values to another source for logging. As shown in FIG. 2, control system 212 preferably includes auxiliary channel 234. Auxiliary channel 234 may be configured to communicate with controller 228 using a PLCbus interface. Controller 228 may transmit unfiltered measurements from sensor 206 to auxiliary channel 234 to be logged on another device, such a laptop for onsite analysis. Such a feature may be used to determine what level filtering of measure values from sensor 206 is necessary. A suitable auxiliary channel includes the Z-World XP8700.

Control system 212 further includes digital output board 232. Digital output board 232 may provide additional digital I/O channels for control system 212. Preferably, controller 228 is configured to send signals to processing tool 226 through digital output board 232. Devices coupled to digital output board may be activated by the transmission of an appropriate signal. Suitable digital output boards include the Z-World XP8120.

Controller 228 is preferably also configured to direct the operation of supply distribution system 208 and return distribution system 210 through signals sent from digital output board 232. By transmitting appropriate signals to supply manifold 209 and return manifold 211, controller 228 is preferably capable of selecting which flows are to be transported to and from sensor 206. Controller 228 may also be configured to transmit signals to pump 216 to pump a selected fluid to and from sensor 206. (For clarity, connections between control system 212 and return and supply distribution systems 210 and 208 are not shown in FIG. 2.) For example, controller 228 may direct the transporting of a first sample flow of the first chemical mixture from first chemical vessel 201 by directing the operation of valves within supply manifold 209 to create a fluid flow path between first chemical vessel 201 and sensor 206. Controller 228 may then direct the operation of pump 216 to transport the first sample flow to sensor 206. Subsequently, controller 228 may direct the operation of valves within return manifold 211 to transport the first sample flow to drain 218 or back to first chemical vessel 201.

As with monitoring system 100, actions of monitoring system 200 are preferably at least partially directed through software. The programming instructions of the software may be at least temporarily stored within storage element 214 of controller 228. Storage element 214 is preferably configured to perform one or more functions that storage element 114 is configured to perform.

Monitoring system 200 may further be configured to detect when an attribute has departed from a desired attribute value range and to provide appropriate notification thereof. In an embodiment, controller 228 is configured to determine whether a first sample concentration is outside of a first sample concentration value range bounded by a low first sample concentration value and a high first sample concentration value. The high and low sample concentration values may represent minimum and maximum preferred values of the first sample concentration attribute. Upon detection that the first sample concentration value is outside of the first sample concentration value range, controller 228 is preferably configured to generate an out-of-tolerance signal for the first sample flow. Controller 228 may be similarly configured for a second sample flow of the second chemical mixture, as well as for other sample flows from the third, fourth, . . . , and nth chemical mixtures. Controller 228's ability to determine whether a measured sample concentration value is out-of-tolerance may be based only on its own ability to analyze measured concentration values received from sensor 206, or may consist of the controller 228 receiving a signal from sensor 206 relating whether a measured concentration is within a desired concentration range.

In an embodiment, the first sample concentration value range is a primary first sample concentration value range, and the low and high first sample concentration values are primary low and high first sample concentration values. Controller 228 may then be configured to determine whether a first sample concentration value is outside of a secondary first sample concentration value range bounded by a secondary low first sample concentration value and secondary high first sample concentration value. The secondary first sample concentration value range is preferably greater than the primary first sample concentration value range. Upon determination that the first sample concentration value is outside the secondary first sample concentration value range, controller 228 is preferably configured to transmit an inhibit signal to processing tool 226. Processing tool 226 is then preferably configured to refrain from using the first chemical mixture in processing upon receipt of the inhibit signal for the first chemical mixture. As was the case above, the ability of controller 228 to determine whether a measured sample concentration value is outside of a secondary sample concentration value range may be based on its own ability to perform such a determination, or on its receiving notification from, e.g., sensor 206 that the measured sample concentration value is outside of the secondary sample concentration value range.

Programming instructions residing at least temporarily in storage element 214 may be used to execute monitoring process 300 to direct the performance of a monitoring sequence on monitoring system 200. The overall execution of monitoring process 300 by monitoring system 200 may be similar to a manner in which monitoring process 300 may be executed by monitoring system 100.

For example, FIG. 4 shows processing steps that may be executed by control system 212 as part of measurement process 308. Execution of processing step 314 preferably directs the transporting of an nth sample flow to sensor 206. Execution of processing step 314 preferably results in controller 228 transmitting appropriate signals to supply distribution system 208 to direct the transporting of the nth sample flow to sensor 206. Such signals may include direction to open and close the necessary supply valves within supply manifold 209 for placing sensor 206 and fluid communication with the nth chemical vessel (e.g., first chemical vessel 201 or third chemical vessel 203). Processing step 314 may further include directing pump 216 to begin pumping the nth sample flow to sensor 206. In an embodiment, pump 216 is a positive displacement pump, and directing pump 216 to begin pumping the nth sample flow to sensor 206 involves sending a sequence of pulses (at, e.g., 80 cycles/min) to activate the pump. Pump 216 may be directed to transport the nth sample flow to sensor 206 at substantially constant flow rate.

As the nth sample flow is transported through sensor 206, sensor 206 may measure an nth sample attribute of the nth sample flow to produce an nth sample attribute value. Preferably, sensor 206 is a concentration sensor configured to measure an nth sample concentration of a first chemical (e.g., a hydrogen peroxide concentration) within the nth sample flow. After measurement, sensor 206 is preferably configured to transmit a measured concentration value to control system 212 (preferably to controller 228) after measurement. Controller 228 may be directed to receive the nth sample concentration value from sensor 206 (step 316). Controller 228 may be configured to determine whether the time since the sensor last transmitted a measured sample attribute value exceeds a max_sensor_wait time (e.g., 100 seconds). If so, controller 228 may be configured to transmit a signal to display unit 236 that the controller failed to receive new data from sensor 206. An out-of-tolerance determination process 320 may also be executed for each nth sample concentration value measured.

Processing step 321 may then be executed to direct the transporting of the nth sample flow from sensor 206. Execution of processing step 321 preferably results in controller 228 transmitting appropriate signals to return distribution system 210 to direct the transporting of the nth sample flow from sensor 206. Such signals may include direction to open and close the necessary return valves within return manifold 211 (e.g., opening the nth return valve and closing other valves) for placing sensor 206 in fluid communication with the nth chemical vessel to allow the nth sample flow to be returned to the nth chemical vessel. Alternately, controller 228 may transmit appropriate signals to direct the opening of and closing of that of the necessary valves within return manifold 211 (e.g., opening drain valve 252 and closing other valves) for placing sensor 206 in fluid communication with drain 218 for disposal of the nth sample flow.

FIG. 5 shows processing steps that may be executed by control system 212 as part of display process 318. In processing step 322, the first numJunk concentration values measured by sensor 206 may be excluded, or dropped. Dropping an initial set of measurements transmitted by sensor 206 may help ensure that the sample concentration values used in calculating a filtered sample concentration value are the most accurate, and may also help synchronize signal transmission between sensor 206 and controller 228. In an embodiment, numJunk is set to three measurements. The filtered nth sample concentration value may then be calculated from the next numMeas nth sample concentration values. In an embodiment, numMeas is set to two measurements. After calculation, the filtered nth sample concentration value may be transmitted to display unit 236 for display (step 326).

FIG. 6 shows processing steps that may be executed by control system 212 as part of out-of-tolerance determination process 320. As stated above, out-of-tolerance determination process 220 may be executed by sensor 206 and/or control system 212. Processing step 328 may determine whether an nth sample concentration value measured by sensor 206 is outside of a primary nth sample concentration value range bounded by a primary low nth sample concentration value and a primary high nth sample concentration value. If the nth sample concentration value is within the primary nth sample concentration value range, out-of-tolerance determination process 320 is preferably exited (processing step 330). If the nth sample concentration value is outside the primary nth sample concentration value range, an out-of-tolerance signal is preferably generated by controller 228 (processing step 332). The out-of tolerance signal may be displayed by display unit 236 to, e.g., warn operators that the nth sample attribute value is outside of a desirable range. Processing step 334 may be performed as described above.

An out-of-tolerance determination process 320 executed by control system 212 preferably also includes processing step 336 for determining whether the nth sample concentration value measured by sensor 206 is outside of a secondary nth sample concentration range bounded by a secondary low nth sample concentration value and a secondary high nth sample concentration value. The secondary nth sample concentration value range is preferably greater than the primary nth sample concentration value range. Upon determining that the nth sample concentration value is outside the secondary nth sample concentration value range, controller 228 preferably generates and transmits an inhibit signal (e.g., a "start inhibit" or a "no-go" signal) to processing tool 226, which is preferably configured to use the first chemical mixture in processing (processing step 340). Processing tool 226 is preferably configured to refrain from using the first chemical mixture in processing upon receipt thereof. If the nth sample concentration value is within a secondary nth sample concentration value range, out-of-tolerance determination process 320 is preferably exited (processing step 338). After exiting out-of-tolerance determination process 320, monitoring process 300 preferably resumes with purge flow process 310.

FIG. 7 shows processing steps that may be executed by control system 212 as part of equipment readiness verification process 304. In processing step 342, it may be determined whether sensor 206 is ready to measure (i.e., ready to begin taking and transmitting measured sample attribute values). Sensor 206 may not be ready to measure because, e.g., it is warming up. If sensor 206 is not ready to measure, processing step 342 is preferably repeated after a predetermined length of time (processing step 344). If sensor 206 is ready to measure, it may then be determined whether processing tool 226 is ready for processing (processing step 346). If processing tool 226 is not ready for processing, monitoring process 300 is preferably exited to, e.g., resolve the problem (processing step 348). If the processing tool is ready for processing, it may then be determined whether the nth chemical vessel is ready for processing. The nth chemical vessel may not be ready for processing because, e.g., it is set up as a spare chemical vessel or it is undergoing a maintenance process. (This information may be communicated by processing tool 226.) In such a case, the execution of monitoring process 300 may be bypassed for the nth chemical vessel (processing step 352), and monitoring process 300 may begin anew with another chemical vessel. In an embodiment in which second chemical vessel 202 is configured as a spare chemical vessel, monitoring process and 300 preferably bypasses the second chemical vessel at processing step 352, and then preferably proceeds with third chemical vessel 203. If the nth chemical vessel is ready for processing, it may then be determined whether a leak or over-temperature condition exists within processing tool 226, or in other components of monitoring system 200 (processing step 354). If such a condition is detected, monitoring process 300 is preferably exited to resolve the problem (processing step 358). Otherwise, monitoring process 300 may proceed with the next process (processing step 356), which is preferably dump flow process 306.

FIG. 8 shows processing steps that may be executed by control system 212 as part of dump flow process 306. Dump flow process 306 is preferably executed prior to measurement process 308. Dump flow process 306 may be used to achieve similar goals with monitoring system 200 as with monitoring system 100. When executing dump flow process 306 by monitoring system 200, processing step 360 is preferably executed to direct the transporting of a nth sample flow of the nth chemical mixture from the nth chemical vessel to sensor 206. The process of transporting the nth sample flow to sensor 206 in dump flow process 306 is preferably similar to the process of transporting the nth sample flow to sensor 206 in measurement process 308. In dump flow process 306, however, the display of measured attribute values of the nth sample flow is preferably suppressed (processing step 362). Such suppression may involve, e.g., sensor 206 not taking sample attribute value measurements during dump flow process 306 or controller 228 ignoring measurement values transmitted by the sensor during the purge flow process. Processing step 364 may then be executed to direct the transporting of the nth sample flow from sensor 206 to drain 218.

FIG. 9 shows processing steps that may be performed as part of purge flow process 310. As with monitoring system 100, purge flow process 310 may be executed for performing a purge flow sequence to remove chemicals remaining after transporting a sample flow through monitoring system 200. In purge flow process 310, purge fluids are preferably transported from purge fluid supply 216 to sensor 206 through supply distribution system 208. As shown in FIG. 2, purge fluid supply 216 preferably includes a N2 purge supply 220 and a DI purge supply 222. Processing step 366 may be executed to direct the transporting of a deionized water flow from the DI purge supply to sensor 206. The deionized water flow may be subsequently transported from sensor 206 to drain 218 (processing step 368). Processing step 370 may be executed to direct the transporting of a nitrogen gas flow from the N2 purge supply to sensor 206. Subsequently, processing step 370 may be executed to direct the transporting of the nitrogen gas flow from sensor 206 to drain 218.

As with monitoring system 100, it may not be necessary to execute dump flow process 306 and purge flow process 310, or either on monitoring system 200. In addition, various durations of these processes may be extended or shortened in view of the particular goals of a monitoring process. And as with monitoring system 100, the constituent processing steps of monitoring process 300 are not required to be executed by monitoring system 200 in the order shown in the Drawings, nor is it required to perform all processes on each loop through the chemical mixtures, or at all.

Figure 10:
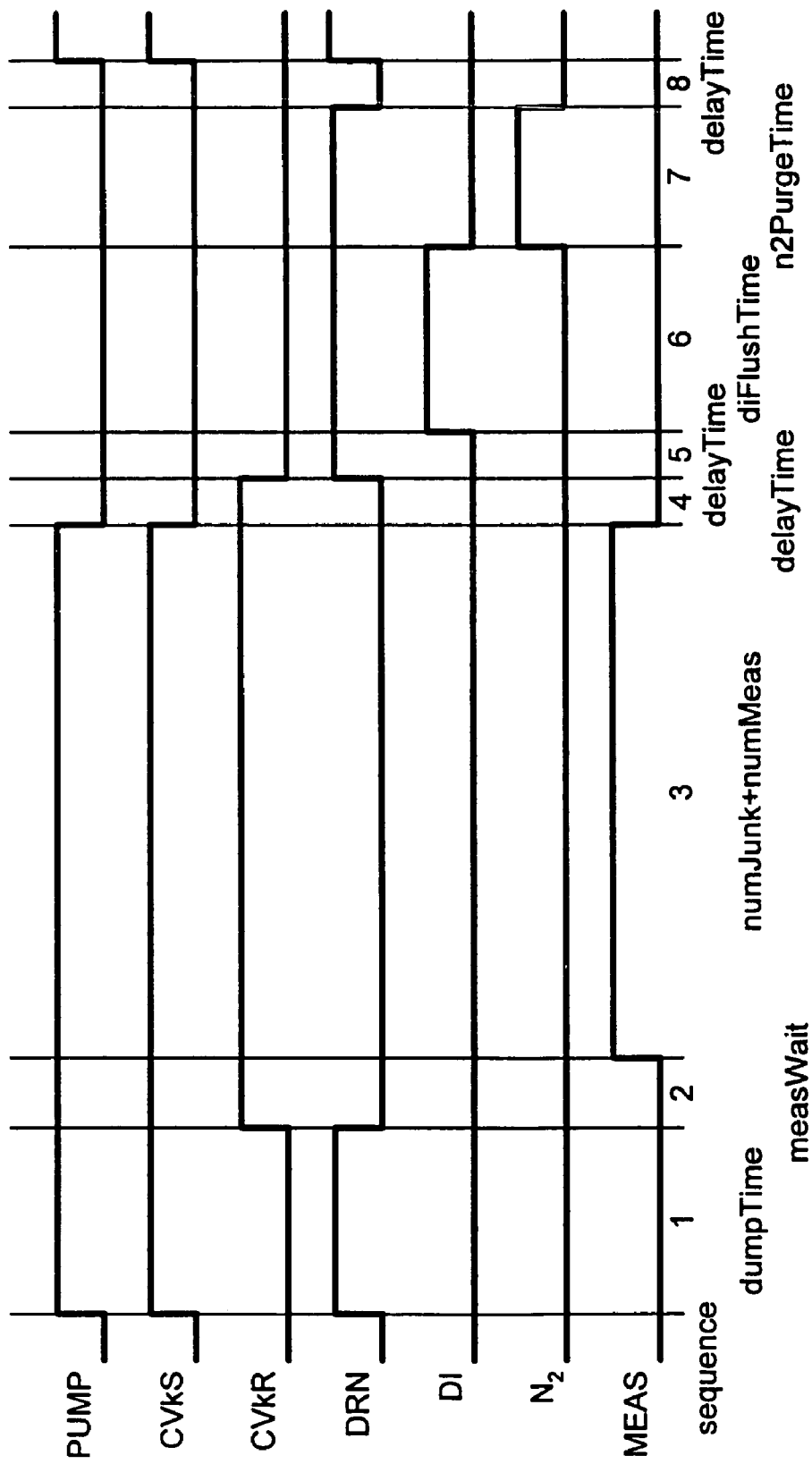
FIG. 10 is a timing diagram showing a sequence of control system outputs during a monitoring process.

FIG. 10 presents a timing diagram showing the operation of various components of monitoring system 200 during the execution of monitoring process 300 for an nth chemical mixture in accordance with an embodiment. The terms along the y-axis of FIG. 10 may represent potential states of various solenoids driving components and/or sub-processes of monitoring system 200 at certain points within monitoring process 300. "High" values are intended to show that a particular device is "on", and "low" values are intended to show the particular device or sub-process is "off".

As shown in FIG. 10, "PUMP" preferably represents the state of pump 216, "CVkS" preferably represents the state of the nth supply valve (e.g., if the second chemical mixture is currently being monitored, then CV2S is the respective supply valve), "CVKR" preferably represents the state of the nth return valve (e.g., if the third chemical mixture is being monitored, then "CV3R" is the respective return valve), "DRN" preferably represents the state of the drain valve 252, "DI" represents the state of DI purge valve 248, and "N2" preferably represents the state of N2 purge valve 246. "MEAS" preferably represents whether control system 212 is actively processing (e.g., accepting and displaying) attribute values measured by sensor 206.

Monitoring process 300 may be conceptually sub-divided into sequences in which various actions are performed. Exemplary sequences are shown on the x-axis. Sequence 1 may performed upon execution of dump flow process 306. Prior to sequence 1, all components shown in FIG. 10 may be "off". At the beginning of sequence 1, the nth supply valve is preferably opened, and pump 216 may be directed begin pumping the nth sample flow to sensor 206. Drain valve 252 may also be opened to direct the nth sample flow to drain 218 after leaving sensor 206. The components are preferably maintained in this condition for a dumpTime (which may be, e.g., about 90 seconds).

Sequences 2, 3, 4, and 5 may be performed upon execution of measurement process 308. At the beginning of sequence 2, drain valve 252 may be close and the nth return valve may be opened. The nth sample flow may then be returned to the nth chemical vessel after leaving sensor 206. The components are preferably maintained in this condition for a measWait period (which may be, e.g., about 50 seconds). Then at the beginning of sequence 3, control system 214 may begin to accept measured sample attribute values from sensor 206 (indicated by MEAS going "on"). As explained above, the control system may drop the first numJunk nth sample attribute values and average the next numMeas nth sample attribute values to produce a filtered nth sample attribute value. Thus, the components are preferably maintained in this condition until numJunk+numMeas nth sample attribute values have been collected. Then at the beginning of sequence 4, the nth supply valve may be closed and pump 216 may cease to transport the nth supply flow to sensor 206. Additionally, control system 214 may cease accepting (or reporting) nth sample attribute values measured by sensor 206 (indicated by MEAS going "off"). After a delayTime (which may be, e.g., about one second), the nth return valve may be closed and drain valve 252 may be opened (sequence 5). The components are preferably maintained in this condition for a second delayTime (which may be, e.g., about one second).

Sequences 6, 7, and 8 may be performed upon execution of purge flow process 610. at the beginning of sequence 6, DI purge valve 248 may be opened to allow deionized water to be transported to sensor 206 and further to drain 218 to purge (i.e., flush) the system. The components are preferably maintained in this condition for a diFlushTime (which may be, e.g., about 5 seconds). Then at the beginning of sequence 7, DI purge valve 248 may be closed and N2 purge valve 246 may be opened to allow nitrogen gas to be transported to sensor 206 and further to drain 218 to purge the system. The components are preferably maintained in this condition for a n2PurgeTime (which may be, e.g., about 5 seconds). At the beginning of sequence 8, N2 purge valve 246 may be closed. The components are preferably maintained in this condition for a delayTime. During the delayTime, monitoring process 300 may begin another monitoring sequence for a new nth chemical mixture. At the end of the delayTime, sequence 1 may begin again for a new nth chemical mixture.

In addition to the ability to monitor one or more attributes of multiple chemical mixtures, monitoring systems as described herein may also employ a variety of process control techniques. Process control techniques may involve using the value of a monitored attribute to determine the extent to which one or more manipulated variables are manipulated to, e.g., adjust the monitored attribute toward a setpoint value (i.e., a desired value). In such a case, the monitored attribute may be considered a controlled attribute. Generally speaking, process control techniques may be implemented in monitoring systems as described herein by inputting one or more measured sample attribute values into a control algorithm. The control algorithm may be used to generate a control output, which may in turn be used to determine the extent of actions taken by the monitoring system on a manipulated variable. The particular value of the control output may determine the extent to which a manipulated variable is manipulated, or whether the manipulated variable will be manipulated at all. Various process control techniques may be used to control attributes monitored by monitoring systems of the present disclosure. The particular control techniques used may in large part depend on the particular attribute being monitored. While exemplary control systems and techniques will be discussed below, other implementations of process control performable by a monitoring system as described herein may be apparent to those skilled in the art having the benefit of this disclosure.

Figure 11:
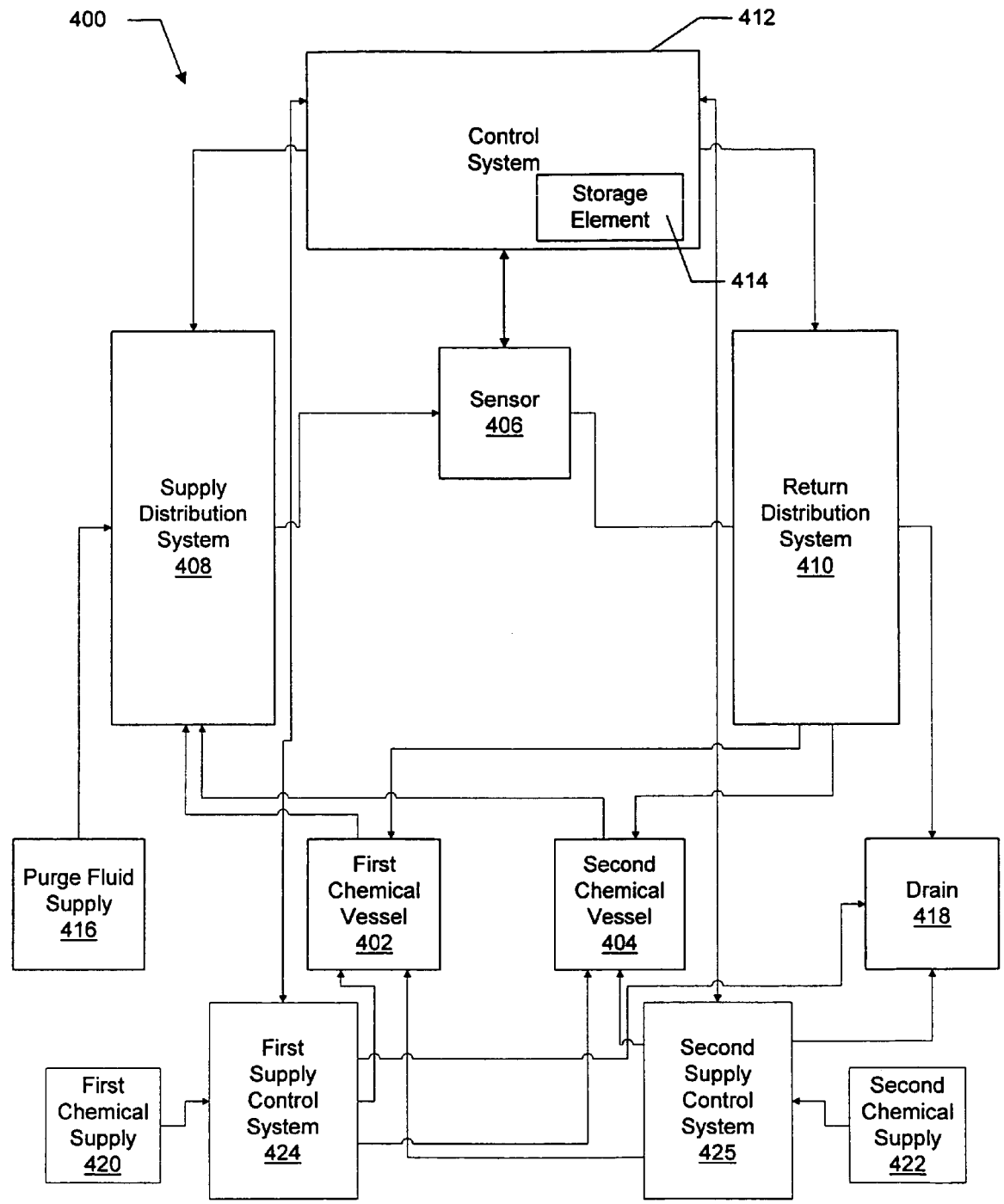
FIG. 11 is a schematic view of a further embodiment of a monitoring system capable of controlling an nth attribute value of an nth chemical mixture.

FIG. 4 presents a schematic view of monitoring system 400. Monitoring system 400 is preferably configured to monitor and control one or more attributes of multiple chemical mixtures contained within multiple chemical vessels. Monitoring system 400 may be configured to perform one or more of the functions that monitoring system 100 may be configured to perform. In the embodiment shown in FIG. 11, monitoring system 400 includes a first chemical vessel 402 and a second chemical vessel 404. First chemical vessel 402 preferably contains a first chemical mixture. Likewise, second chemical vessel 404 preferably contains a second chemical mixture. In addition, monitoring system 400 preferably includes sensor 406. Sensor 406 is preferably configured to selectively receive a first sample flow of the first chemical mixture from the first chemical vessel and to selectively receive a second sample flow of the second chemical mixture from the second chemical vessel. Sensor 406 is preferably configured to measure a first sample attribute of the first sample flow and a second sample attribute of the second sample flow. Monitoring system 400 further preferably includes supply distribution system 408 and return distribution system 410. Supply distribution system 408 is preferably configured to selectively transport the first sample flow of the first chemical mixture from first chemical vessel 402 to sensor 406. Return distribution system 410 is preferably configured to selectively transport the first sample flow of the first chemical mixture from sensor 406 to first chemical vessel 402 or to drain 418. Monitoring system 400 further preferably includes a purge fluid supply 416 and a drain 418. In addition, monitoring system 400 preferably includes control system 412 having a storage element 414.

Components of monitoring system 400 may be configured to perform one or more of the functions that their numerically respective counterparts of monitoring system 100 may be configured to perform. For example, sensor 406 may be configured to perform one or more of the functions that sensor 106 may be configured to perform, and control system 412 may be configured to perform one or more of the functions that control system 112 may be configured to perform.

Monitoring system 400 further includes additional components to aid in the implementation of process control techniques. For example, monitoring system 400 preferably includes first chemical supply 420 and second chemical supply 422. First chemical supply 420 and second chemical supply 422 preferably represent sources of a first chemical and a second chemical, respectively. The first chemical and second chemical are each preferably constituent chemicals of the chemical mixtures monitored by monitoring system 400. In an embodiment in which the first, second, third, and forth chemical mixtures are SC1 mixtures, the first and second chemical supplies may each be any one of water, hydrogen peroxide, or ammonium hydroxide. The first and second chemical supplies may supply pure chemicals or mixtures of chemicals containing the first and second chemicals.

Monitoring system 400 may further include a first supply control system 424 and second supply control system 425. First supply control system 424 preferably is configured to control the amount of the first chemical that is supplied from first chemical supply 422. Likewise, second supply control system 425 is preferably configured to control the amount of the second chemical that is supplied from second chemical supply 422. First and second supply control systems 424 and 425 may include a variety of devices to respectively control the supply of first and second chemicals, including, but not limited to, valves, pumps, and mass flow controllers. The first and second supply control systems are preferably configured to receive signals from control system 412 to direct the amount of the first and second chemicals, respectively, that are supplied as part of the control process. The first and second supply control systems are preferably configured to independently control the amount of the first and second chemical, respectively, supplied to each chemical vessel, and thus to the chemical mixtures within each chemical vessel. For example, first supply control system 424 may supply a given amount of the first chemical to second chemical vessel 404 upon receiving an appropriate signal from control system 412, but not transport any chemical at all to first chemical vessel 402. Furthermore, each supply control system may simultaneously supply a respective chemical to multiple chemical vessels monitored by monitoring system 400, and may supply each respective chemical at different rates for each chemical vessel being supplied at a given time.

First and second supply control systems 420 and 422 may be configured to supply the first and second chemicals, respectively, to chemical vessels monitored by monitoring system 400 in a variety of manners. For example, the first and second supply control systems may be configured to be in fluid communication with return distribution system 410, which may be adapted to deliver the first and second chemicals to a chemical vessel. In another embodiment, the first and second supply control systems may each be coupled directly to each chemical vessel, and may both contain mechanisms for determining which chemical vessel flow is directed into. In addition, first and second supply control systems 420 and 422 are preferably configured to transmit to control system 412 information concerning, e.g., the rate at which they are supplying chemicals to the chemical vessels monitored by monitoring system 400. Such information may be transmitted as analog signals, which may then be converted into digital signals to be used by control system 414. Consequently, control system 414 may further include an analog-to-digital converter to convert such analog signals into digital signals. First and second chemical supply systems 420 and 422 may also each be configured to transport the first and second chemicals, respectively, to drain 418 to, e.g., establish flow from the first and second chemical supplies, respectively, prior to transporting the chemicals to a chemical vessel.

In addition to being configured to perform one or more of the functions of control system 112, control system 412 may be further configured to direct one or more control processes. Preferably, control system 412 is configured to execute several sets of programming instructions to direct the operation of one or more control sequences performed by monitoring system 400. The programming instructions may at least temporarily reside in storage element 414. Processing steps by which such programming instructions may direct the operation of monitoring system 400 (including the execution of any control processes) are shown in FIGS. 14–19.

Figure 14:
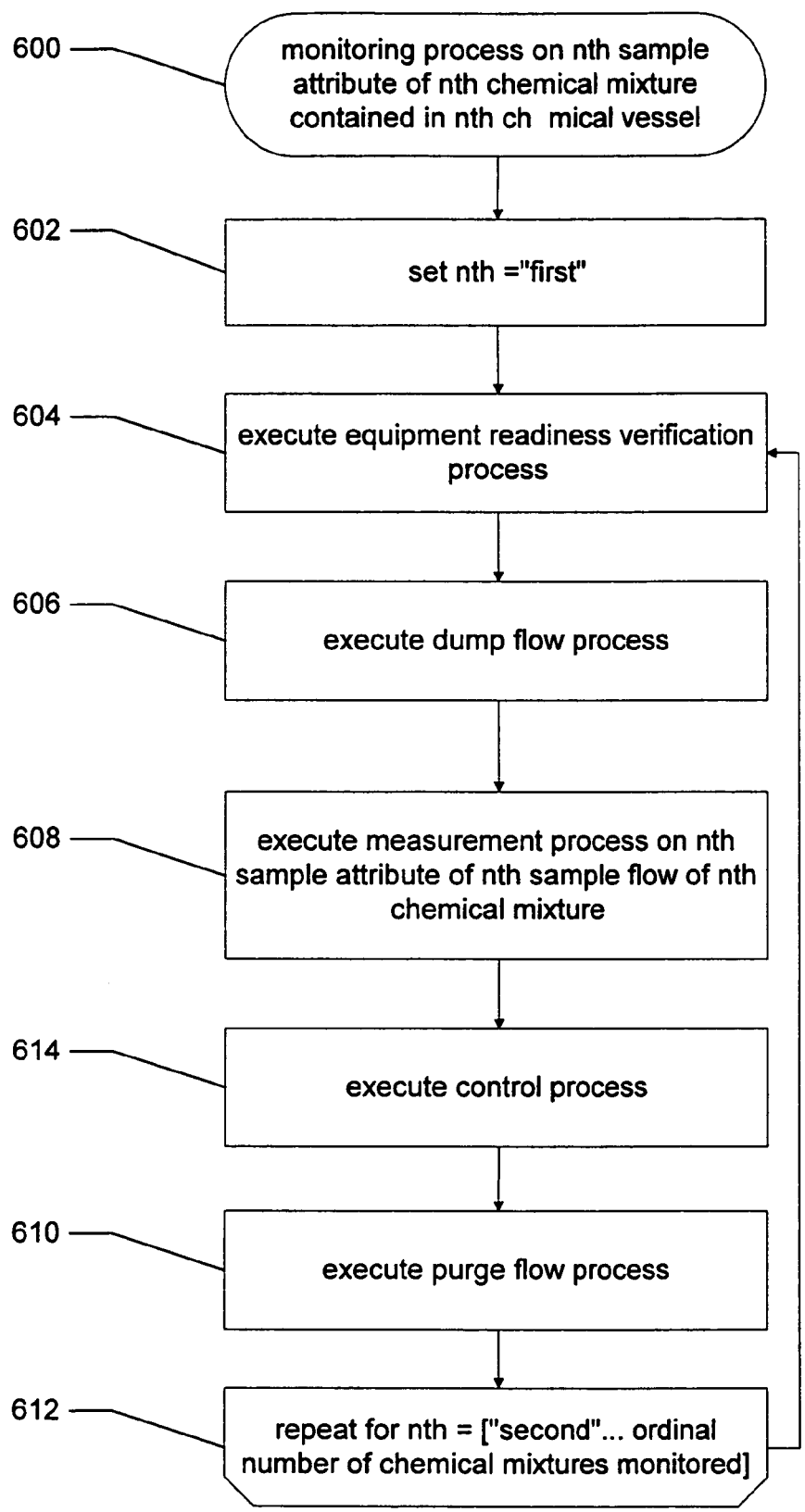
FIG. 14 is a flow diagram of a monitoring process for monitoring an nth sample attribute of an nth chemical mixture in accordance with a further embodiment, in which the process may include a control process for controlling an nth bulk attribute of the nth chemical mixture.

As shown in FIG. 14, the processing steps preferably include monitoring process 600. Monitoring process 600 may be configured to perform one or more of the functions that monitoring process 300 may be configured to perform. Monitoring process 600 is preferably configured to monitor an nth sample attribute of an nth chemical mixture contained in an nth chemical vessel. Monitoring process 600 is further preferably configured to control the value of the nth bulk attribute.

Monitoring process 600 preferably initiates monitoring with the first chemical mixture by setting nth equal to "first" (step 602) so that monitoring process 600 will be carried out on the first chemical mixture. Monitoring process 600 then preferably executes processing step 604, an equipment readiness verification process. Subsequently, a dump flow process may be executed as processing step 606. A measurement process may then be executed as processing step 608. Then measurement process 608 is preferably executed for the nth sample attribute of the nth sample flow of the nth chemical mixture. Subsequently, purge flow process 610 may be executed. Processing steps 602, 604, 606, 608, and 610 may be configured to perform upon execution one or more of the functions that their numerical counterparts in monitoring process 300 (i.e., processing steps 302, 304, 306, 308, and 310, respectively) may be configured to perform. Along similar lines, processing steps 602, 604, 606, 608, and 610 may contain sub-processing steps that may be configured to perform one or more of the functions that sub-processing steps of processing steps 302, 304, 306, 308, and 310, respectively, may be configured to perform.

Monitoring process 600 preferably further includes control process 614. Control process 614 is preferably executed after measurement process 608 and before purge flow process 610. Processing steps 604, 606, 608, 610, and 614 may be repeated for nth=["second" . . . the ordinal number of chemical mixtures monitored] (step 612). That is, the processing steps of monitoring process 600 may be repeated for a second chemical mixture, a third chemical mixture, a fourth chemical mixture, etc., until the process has been repeated for all chemical mixtures being monitored by monitoring system 400. Additionally, a termination signal may be sent to control system 412 at any point within monitoring process 600 to terminate the process.

The above-described processing steps, which may be executable by control system 412, preferably direct the performance of appropriate operational sequences within monitoring system 400. For example, executing monitoring process 600 preferably results in the performance of a monitoring sequence on an nth sample attribute of an nth sample flow of the nth chemical mixture. The monitoring sequence preferably includes performing an equipment readiness verification sequence upon execution of equipment readiness verification process 604, performing a dump flow sequence upon execution of dump flow process 606, performing a measurement sequence upon execution of measurement process 608, performing a control sequence upon execution of control process 614, and performing a purge flow sequence upon execution of purge flow process 610. Control system 412 is preferably configured to direct the repetition of the above-described sequences as directed by the programming instructions.

Control process 614 may involve the execution of programming instructions to implement a variety of process control techniques. For example, control process 614 may involve feedback and/or feed forward control. Furthermore, control process 614 may implement proportional, integral, and derivative control algorithms, as well as any combinations thereof. Settings for a control algorithm of control process 614 may determined in a variety of ways, including the use of data obtained during monitoring processes.

Figure 15:
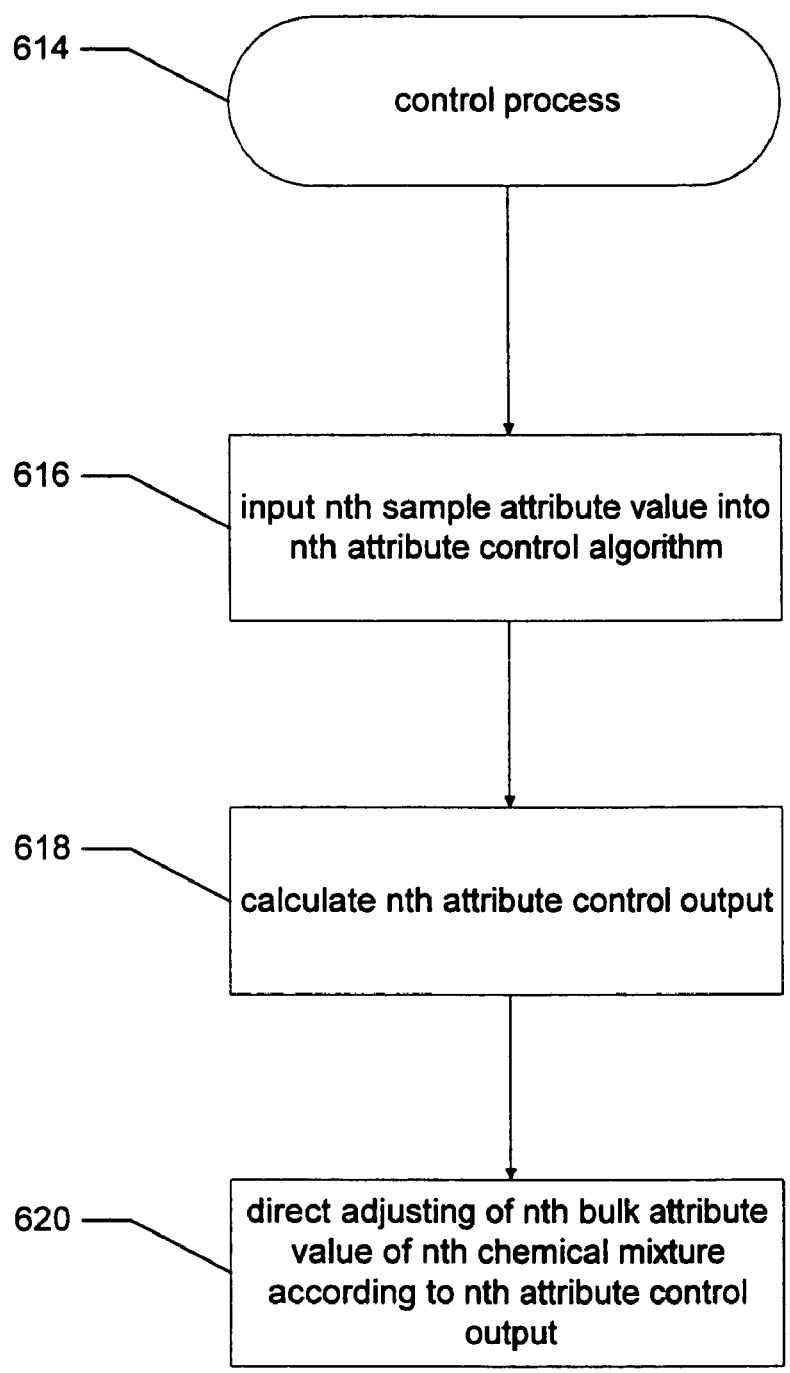
FIG. 15 is a flow diagram of a control process executable in the monitoring process shown in FIG. 14.

Processing steps of an exemplary implementation of control process 614 is shown in FIG. 15. Control process 614 is preferably configured to maintain the value of the nth bulk attribute of the nth chemical mixture at or near an nth attribute setpoint value. As measurement process 608 may be configured similarly to measurement process 308, execution of measurement process 608 preferably results in measurement of an nth sample attribute value of an nth sample flow from an nth chemical mixture. The nth sample attribute value may then be used in control process 614. By comparing the nth sample attribute value to the nth attribute setpoint value, it may be determined how far the nth bulk attribute value is below a desired level at a particular instance. That information may then be used to determine the extent to which the nth bulk attribute should be adjusted toward the nth attribute setpoint value. As the nth sample attribute value is preferably representative of the nth bulk attribute value, changes in the nth bulk attribute value may be quickly reflected in the nth sample attribute value. Thus when the nth sample attribute value is at or near the nth attribute setpoint value, it may be reasoned that the nth bulk attribute value is also at or near the nth attribute setpoint value.

As part of control process 614, the nth sample attribute value measured in measurement process 608 may be input into an nth attribute control algorithm (processing step 616). The nth sample attribute is preferably a filtered nth sample attribute value. To produce the filtered nth sample attribute value, measurement process 608 may include a display process configured similarly to display process 318 to produce the filtered nth sample attribute value. The nth attribute control algorithm preferably is composed of a step or set of steps used to generate an appropriate nth attribute control output for a measured nth sample attribute value. The nth attribute control algorithm may be any of a variety of control algorithms. Furthermore, the nth attribute control algorithm may utilize multiple sample attribute values measured by sensor 406. Additionally, the nth attribute control algorithm may include multiple control algorithms capable of using multiple attribute values to generate multiple control outputs.

Upon receiving appropriate inputs, nth attribute control output calculation process 618 may be executed. The nth attribute control output may be used to determine an appropriate control response. For example, nth attribute control outputs within a certain range of values may result in no control response being taken. Alternatively, nth attribute control outputs within other ranges of values may result in certain actions been taken by components of monitoring system 400 to adjust the value of one or more attributes toward setpoint values. Subsequent to the calculation of the nth attribute control output, execution of control process 614 preferably directs the adjusting of an nth bulk attribute value of the nth chemical mixture according to nth attribute control output (processing step 620). Depending on the control output, directing the adjusting of the nth bulk attribute value may include directing the increasing of the nth bulk attribute value, directing the decreasing of the nth bulk attribute value, or taking no control action on the nth bulk attribute value.

The nth attribute is preferably one that may be controlled by the addition of a chemical to the nth chemical mixture. The added chemical is preferably one of the constituent chemicals of the nth chemical mixture. Thus, the amount of chemical added to the nth chemical mixture when adjusting the nth bulk attribute value may be considered a manipulated variable. Suitable nth attributes for control by control process 614 include concentrations of chemicals within the nth chemical mixture, as well as other attributes such as resistivity. If, for example, the nth sample attribute is the concentration of a first chemical within the nth sample flow, then the nth bulk attribute value may be increased by adding more of the first chemical or decreased by adding more of other constituent chemicals of the nth chemical mixture. Likewise, if the nth sample attribute is the concentration of a second chemical within the nth sample flow, then the nth sample attribute may be increased by adding more of the second chemical or decreased by adding more of other constituent chemicals of the nth chemical mixture. In an embodiment in which the chemical mixtures are SC1 solutions and the nth attribute is a hydrogen peroxide concentration, then the second chemical may be, e.g., ammonium hydroxide or water. The nth chemical mixture may be drained during the adding of a chemical to, e.g., maintain the total chemical mixture volume below a certain level. The amount of chemical added as part of the adjusting process may then be adjusted accordingly.

Figure 16:
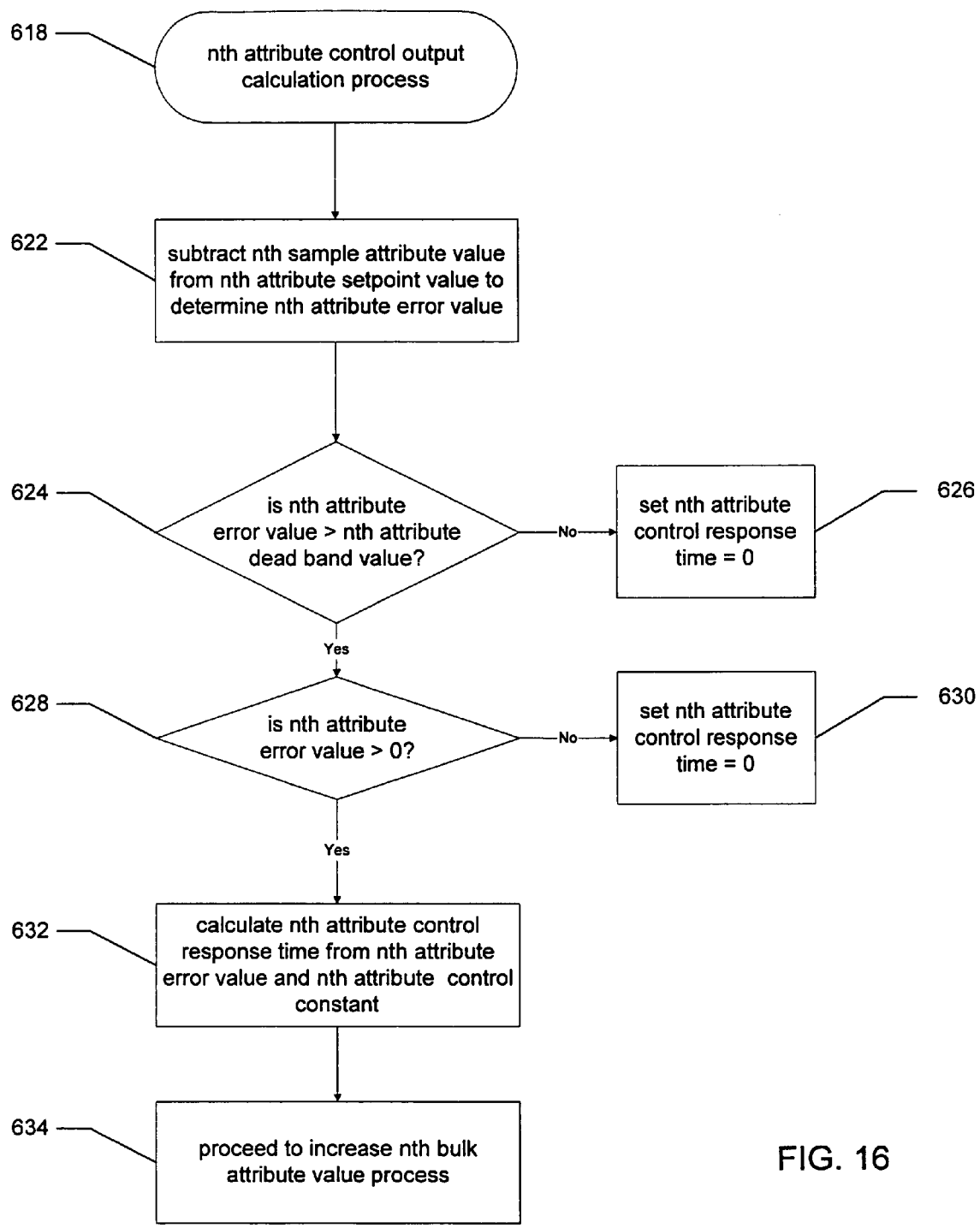
FIG. 16 is a flow diagram of a nth attribute control output calculation process executable in the control process shown in FIG. 15.

FIG. 16 shows processing steps that may be executed as part of nth attribute control output calculation process 618. Control output calculation process 618 is preferably configured to employ an nth attribute control algorithm to determine an nth attribute control output. The nth attribute control algorithm may be a proportional gain algorithm with an adjustment for dead time. Additionally, the nth attribute control algorithm may be any of a variety of control algorithms, some of which will be apparent to those skilled in the art having the benefit of this disclosure. The nth attribute control output may include instructions to undertake processes that increase or decrease the nth bulk attribute value, or take no action on the nth bulk attribute value at all. However, the nth attribute control output is not necessarily a signal generated by nth attribute control algorithm, but may also be, e.g., a sequence or command within the programming instructions that results in the execution of an adjusting process appropriately configured to the value of the control output.

As stated above, increasing or decreasing the nth bulk attribute may be accomplished by adding a quantity of a chemical (preferably a constituent chemical of the nth chemical mixture) to the nth chemical mixture. The amount of the chemical to be added may be calculated by determining the length of time for which the chemical should be transported to the nth chemical mixture at a given flow rate. Such a time may be considered an nth attribute control response time. Once it is decided that the nth attribute should be increased or decreased, the nth attribute control response time is preferably configured such that after the chemical is supplied to the nth chemical mixture for the nth attribute control response time, the value of the nth bulk attribute within the nth chemical mixture is preferably at or near a desired level. Such a process may be referred to as "spiking". When no action is to be taken on the nth bulk attribute value, the nth attribute control response time may be set to zero.

As part of nth attribute control output calculation process 618, an nth attribute error value may be determined from the nth attribute value and nth attribute setpoint value (processing step 622). The nth attribute setpoint value is preferably a desired value of the nth sample attribute. The nth attribute setpoint value may be the mean of a low nth sample attribute values and a high nth sample attribute value used in, e.g., an out-of-tolerance determination process. The nth attribute error value is preferably determined by subtracting the nth sample attribute value from the nth attribute setpoint value to produce the nth attribute error value.

It may then be determined whether the nth attribute error value is greater than an nth attribute dead band value (processing step 624). The nth attribute dead band value may be a level of the nth attribute error value from which no control response will be taken. If it is desired that, for example, a control response is always taken upon a calculation of a non-zero nth attribute error value, the nth attribute dead band value may be set at or very near zero. If the nth attribute error value is not greater than the nth attribute dead band value, then the nth attribute control response time may be set to zero (processing step 626). If the nth attribute error value is greater than the nth attribute dead band value, it may then be determined whether the nth attribute error value is greater than zero (processing step 628).

Processing step 628 may be most useful in situations where nth attribute error values are most often generated by nth sample attribute values falling below nth attribute setpoint values (e.g., by degrading or evaporating). In such situations, the occurrence of nth sample attribute values going above the nth attribute setpoint value may be an undesirable situation that should not be controlled away, but monitored. In addition, it may be undesirable in some processes to take actions that would reduce the nth sample attribute value, such as adding more of other constituent chemicals within the nth chemical mixture to reduce an nth sample concentration value. If the nth attribute error value is not greater than zero, then the nth attribute control response time is preferably set to zero (processing step 630). If the nth attribute error value is greater than zero, then an nth attribute control response time may be calculated (processing step 632).

Numerous methods may be used for determining a nth attribute control response time. In an embodiment, the nth attribute control response time may be calculated by multiplying the nth attribute error value and an nth attribute control constant. The nth attribute control constant may determined during testing of each chemical supply system at various flow rates. Preferably, the nth attribute control constant is configured such that multiplying it with an nth attribute error value will produce a desired nth attribute control response time. The nth attribute control response time calculated in processing step 632 is preferably configured for a process to increase the nth bulk attribute value. For example, if the nth attribute is a first chemical concentration, then the nth attribute control response time may be the time for which a first chemical supply flow should be transported to the nth chemical vessel to introduce an amount of the first chemical to the nth chemical mixture sufficient to increase the bulk first chemical concentration within the nth chemical mixture. After calculation of the nth control response time, control process 614 preferably proceeds to a processing step to increase the nth bulk attribute value (processing step 634).

Processes for increasing or decreasing the nth bulk attribute may be executed as part of directing the adjusting of the nth bulk attribute value (processing step 620). If the nth attribute control algorithm calculation process 618 results in processing step 634 being executed, then a process to increase the nth bulk attribute is preferably executed as part of processing step 620. In an embodiment in which the nth sample attribute is an nth sample concentration of a first chemical within the nth sample flow, increasing the nth bulk attribute preferably involves performing a first chemical supply sequence for the nth attribute control response time.

Figure 17:
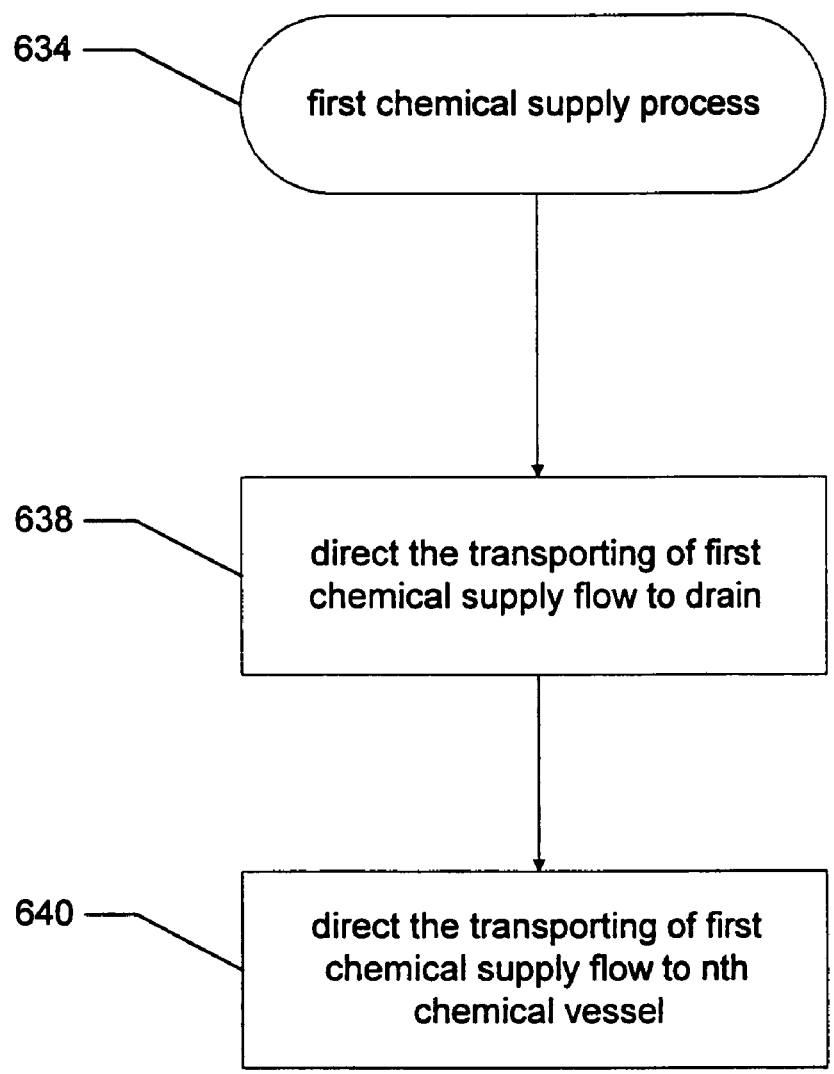
FIG. 17 is a flow diagram of a first chemical supply process executable from the nth attribute control output calculation process shown in FIG. 16.

FIG. 17 shows processing steps that may be executed as part of first chemical supply process 634. Upon execution of processing step 640, control system 414 preferably directs the transporting of a first chemical supply flow of the first chemical from first chemical supply 420 to the nth chemical vessel. In addition, control system 414 preferably directs first chemical supply system 424 to transport the first chemical supply flow to the nth chemical vessel for the nth attribute control response time. The first chemical supply flow is preferably transported to the nth chemical vessel for the nth control response time at a flow rate sufficient to increase the nth bulk attribute value to a level substantially equal to (i.e., at or near) the nth attribute setpoint value.

Prior to transporting the first chemical supply flow to the nth chemical vessel, though, control system 414 preferably directs the transporting of a first chemical supply flow to drain 418 (processing step 638). Control system 414 may direct the first chemical supply system to transport the first chemical to the drain for a pre-control response time to establish flow within the piping system from first chemical supply 420. The pre-control response time may be relatively short (e.g., three seconds).

First chemical supply process 634 is preferably performed concurrently with transporting the nth sample flow to the nth chemical mixture. In an embodiment in which the first chemical is supplied to the nth chemical vessel through return distribution system 410, supplying the first chemical to the nth chemical vessel concurrently with the transporting the nth sample flow to the nth chemical vessel may allow the first chemical supply flow to begin mixing with the nth sample flow prior to being introduced to the nth chemical vessel.

Figure 19:
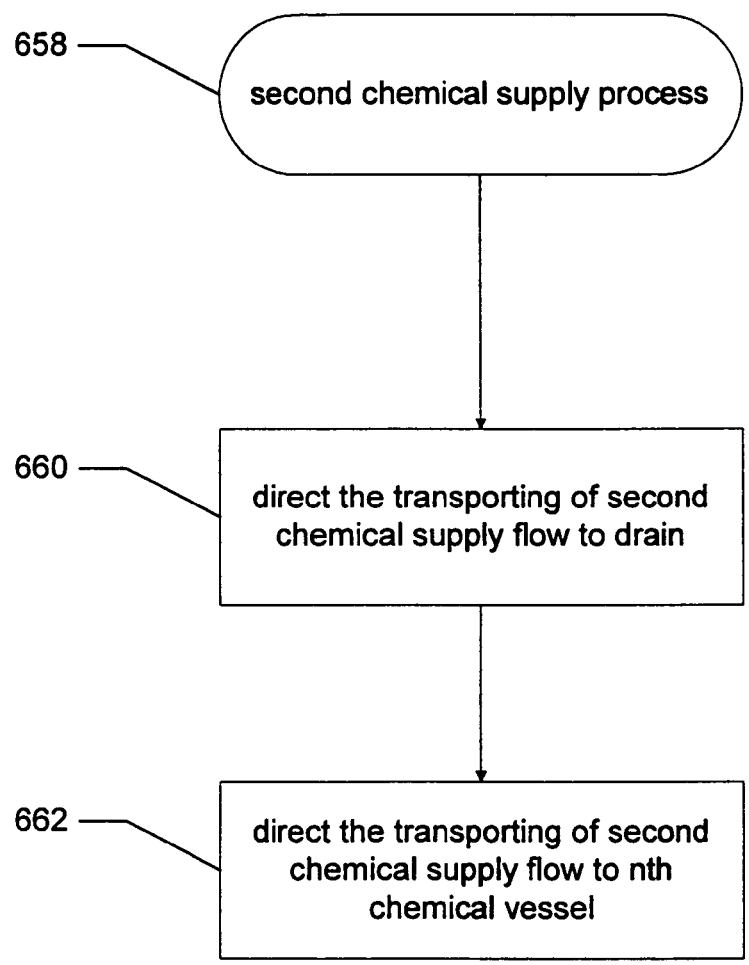
FIG. 19 is a flow diagram of a second chemical supply process executable from the nth attribute control output calculation process shown in FIG. 18.

Similarly, if the nth sample attribute is an nth sample concentration of a second chemical within the nth sample flow, increasing the nth bulk attribute preferably involves performing a second chemical supply sequence for the nth attribute control response time. FIG. 19 shows processing steps that may be executed as part of second chemical supply process 658. Upon execution of processing step 662, control system 414 preferably directs the transporting of a second chemical supply flow of the second chemical from second chemical supply 422 to the nth chemical vessel. In addition, control system 414 preferably directs second chemical supply system 425 to transport the second chemical supply flow to the nth chemical vessel for the nth attribute control response time. The second chemical supply flow is preferably transported to the nth chemical vessel for the nth control response time at a flow rate sufficient to increase the nth bulk attribute value to a level substantially equal to (i.e., at or near) the nth attribute setpoint value.

Prior to transporting the second chemical supply flow to the nth chemical vessel, though, control system 414 preferably directs the transporting of a second chemical supply flow to drain 418 (processing step 660). Control system 414 may direct the second chemical supply system to transport the second chemical to the drain for a pre-control response time to establish flow within the piping system from second chemical supply 422. The pre-control response time may be relatively short (e.g., three seconds).

Second chemical supply process 634 is preferably performed concurrently with transporting the nth sample flow to the nth chemical mixture. In an embodiment in which the second chemical is supplied to the nth chemical vessel through return distribution system 410, supplying the second chemical to the nth chemical vessel concurrently with the transporting the nth sample flow to the nth chemical vessel may allow the second chemical supply flow to begin mixing with the nth sample flow prior to being introduced to the nth chemical vessel.

As stated above, monitoring process 600 may be capable of implementing control processes for multiple nth attributes. The multiple nth attributes may include the respective concentrations of multiple chemicals within the nth chemical mixture. For example, monitoring process 600 could monitor a sample concentration of a first chemical and a sample concentration of a second chemical within the nth sample flow and then input those sample concentration values into respective control algorithms to produce respective control outputs. The monitoring process 600 may then direct the delivery of the first and second chemical supply flow to the nth chemical mixtures as dictated by the control algorithm for each controlled concentration. For example, the concentration of the first chemical within the nth sample flow may be such that no control response is required for that attribute, while at the same time the concentration of the second chemical may be such that it is desirable to add a quantity of the second chemical to the nth chemical mixture to increase the bulk concentration of the second chemical within the nth chemical mixture.

However, concentration values of both a first chemical and a second chemical may reach levels sufficient to warrant adding quantities of both the first and second chemical to the nth chemical vessel. As described above, the first and second chemicals may at some point be transported over the same line to be introduced into the nth chemical vessel. It may be undesirable, though, to mix the first and second chemicals prior to their introduction into the nth chemical vessel. Consequently, control process 614 is preferably executed for each controlled concentration on separate repetitions of monitoring process 600 for a particular chemical mixture. For instance, on one cycle of monitoring process 600 for a nth chemical mixture, control process 614 may be executed for the concentration of a first chemical within the nth chemical mixture, and on the subsequent cycle for that nth chemical mixture, control process 614 may be executed for the concentration of a second chemical within the nth chemical mixture. Such a sequence may help ensure that the first and second chemicals do not mix before entering the nth chemical vessel. Of course, if the first and second chemical supply flows do not share the same flow lines at any point within monitoring system 400, the sequencing of control processes for each chemical concentration monitored may not be necessary.

Figure 18:
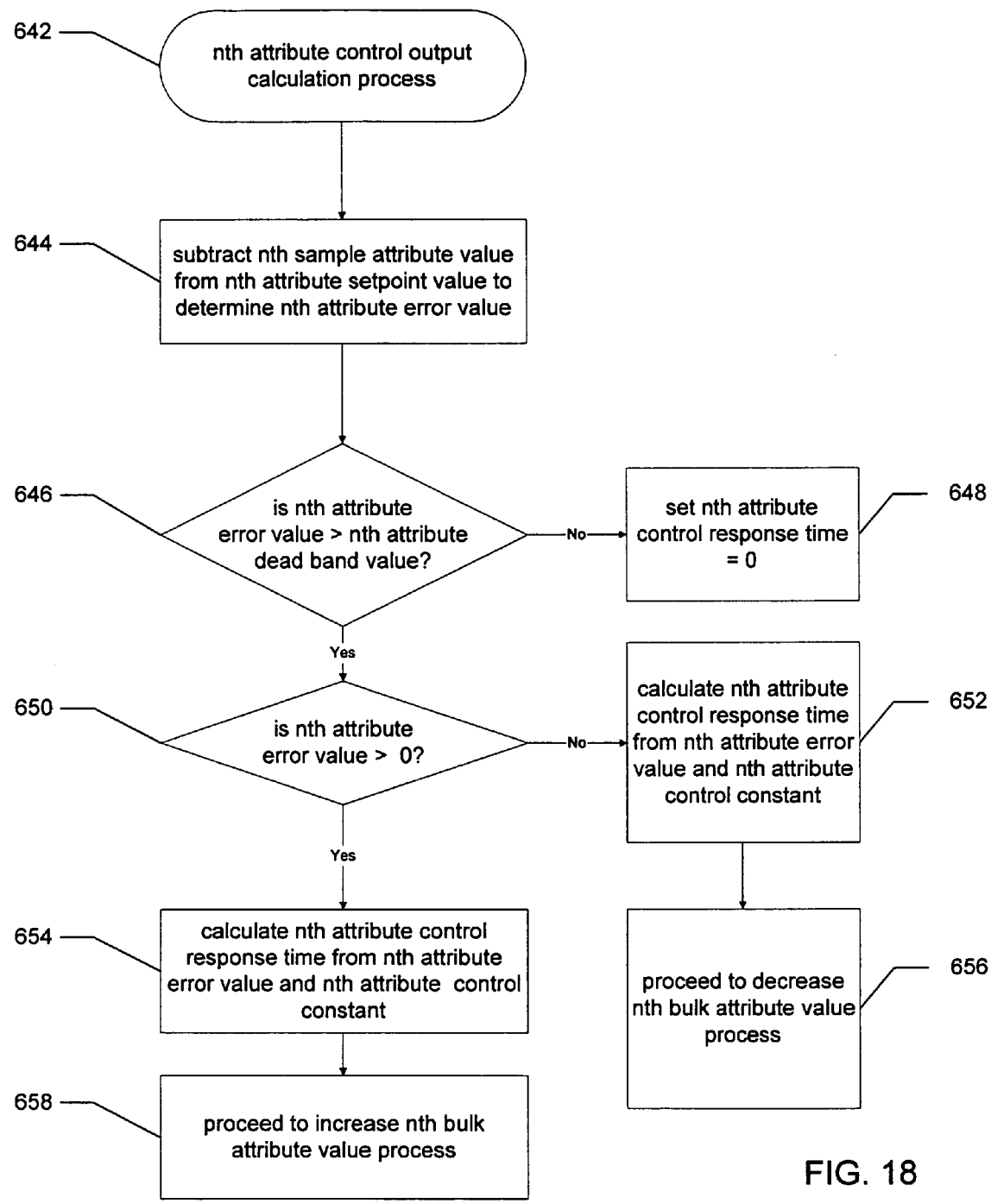
FIG. 18 is a flow diagram of a nth attribute control output calculation process executable in the control process shown in FIG. 15.

Although control output calculation process 618 is preferably configured to produce a control output that results in the nth bulk attribute being adjusted only by a process that increases the nth bulk attribute, it may also be desirable to implement a control output calculation process capable of producing control outputs that may result in the nth bulk attribute being adjusted by both increasing and decreasing the nth bulk attribute value. FIG. 18 shows processing steps that may be executed as part of nth attribute control output calculation process 642. Control output calculation process 642 is preferably configured to determine an nth attribute control output. Several processing steps of nth attribute control output calculation process 642 may be configured similarly to several respective processing steps of nth attribute control output calculation process 618. Preferably, processing steps 644, 646, and 648 may be configured to perform one or more of the functions that processing steps 622, 624, and 626, respectively, may be configured to perform.

Differences between nth attribute control output calculation process 642 and nth attribute control output calculation process 618 may be seen at processing step 650. If it is determined that the nth attribute error value is greater than zero, than processing steps 654 and 658 may be executed. Processing steps may be configured to perform one or more of the functions that processing steps 632 and 634, respectively, may be configured to perform. If, however, it is determined that the nth attribute error value is not greater than zero, then a nth attribute response time may be calculated for a process to decrease the nth bulk attribute value (processing step 652). For example, if the nth attribute is a first chemical concentration, then the nth attribute control response time may be the time for which a second chemical supply flow should be transported to the nth chemical vessel to introduce an amount of the second chemical to the nth chemical mixture sufficient to decrease the bulk first chemical concentration within the nth chemical mixture. After calculation of the nth attribute control response time in processing step 652, control process 614 preferably proceeds to a processing step to decrease the nth bulk attribute value (processing step 656).

Increasing the nth bulk attribute value preferably involves executing a supply process for a chemical whose addition to the nth chemical mixture will decrease the nth bulk attribute value. For example, if the nth attribute is a concentration of a first chemical, then decreasing the nth bulk attribute preferably involves performing a second chemical supply sequence. Performance of the second chemical supply sequence may be directed by executing second chemical supply process 658. Conversely, if the nth attribute is a concentration of a second chemical, then decreasing the nth bulk attribute preferably involves performing a first chemical supply sequence. Performance of the first chemical supply sequence may be directed by executing first chemical supply process 634.

Figure 12:
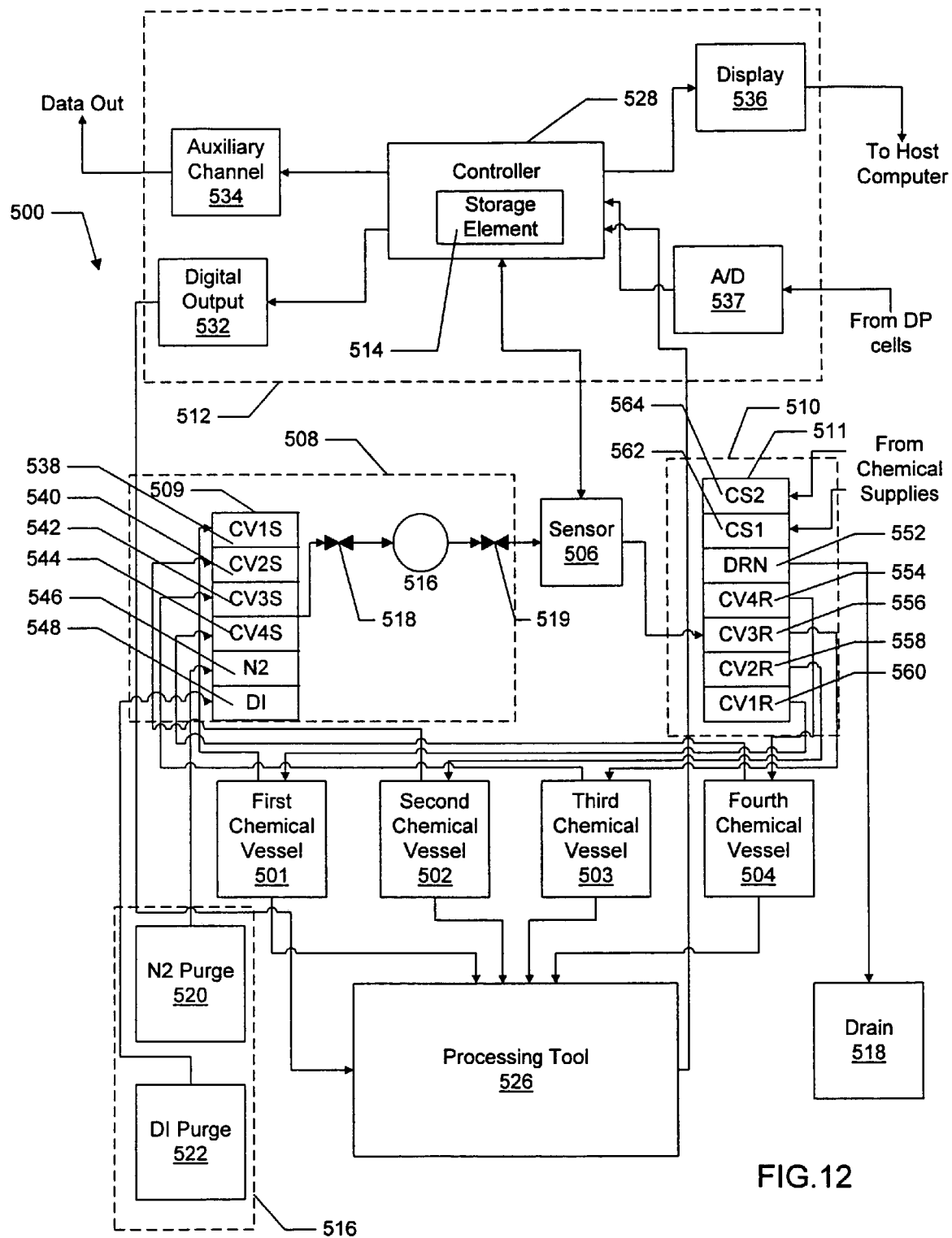
FIG. 12 is a schematic view of a further embodiment of a monitoring system capable of controlling an nth attribute value of an nth chemical mixture.
Figure 13:
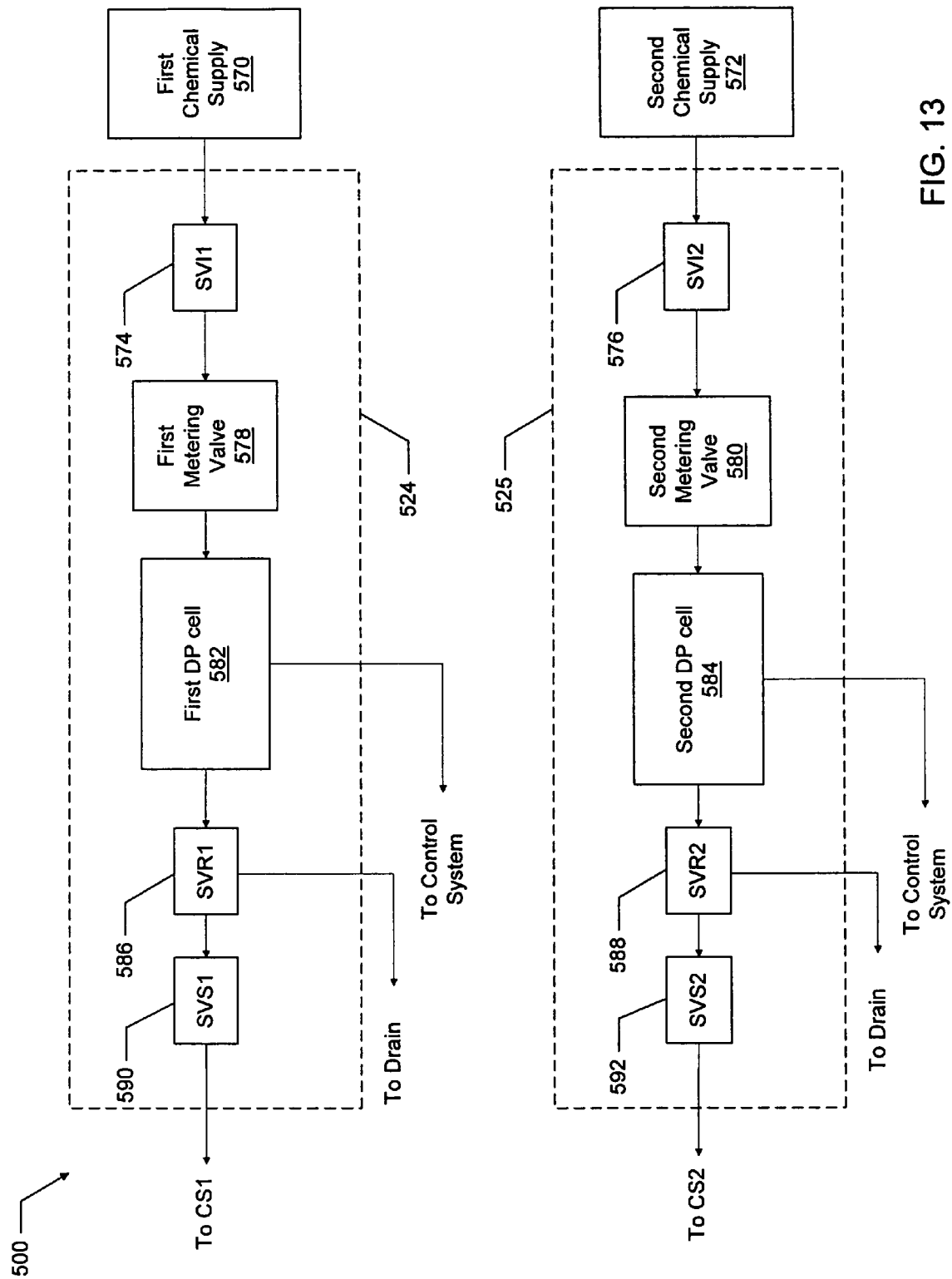
FIG. 13 is a schematic view of first and second chemical supplies and first and second chemical supply systems of the monitoring system shown in FIG. 12.

FIGS. 12 and 13 together present a schematic view of monitoring system 500. Monitoring system 500 may be configured to perform one or more of the functions that monitoring system 200 may be configured to perform. Monitoring system 500 is preferably configured to monitor one or more attributes of multiple chemical mixtures contained in multiple chemical vessels. As shown in FIG. 12, monitoring system 500 preferably includes a first chemical vessel 501, a second chemical vessel 502, a third chemical vessel 503, and a fourth chemical vessel 504. First chemical vessel 501 preferably contains a first chemical mixture. Likewise, second, third, and fourth chemical vessels 502, 503, and 504 preferably contain second, third, and fourth chemical mixtures, respectively. In addition, monitoring system 500 preferably includes sensor 506. Sensor 506 is preferably configured to selectively receive a first sample flow of the first chemical mixture from the first chemical vessel, a second sample flow of the second chemical mixture from the second chemical vessel, a third sample flow of the third chemical mixture from the third chemical vessel, and a fourth sample flow of the fourth chemical mixture from the fourth chemical vessel. Preferably, sensor 506 is configured to measure a first sample attribute of the first sample flow, a second sample attribute of the second sample flow, a third sample attribute of the third sample flow, and a fourth sample attribute of the fourth sample flow. By multiplexing multiple sample flows through sensor 506, monitoring system 500 may monitor an attribute of multiple chemical mixtures without having to use separate sensors for each chemical monitored.

Monitoring system 500 may further include processing tool 526. Processing tool 526 may be a machine, apparatus, or the like configured for use in chemical processing. Preferably, processing tool 526 is configured for use in semiconductor fabrication processes. Processing tool 526 preferably is configured to use the first, second, third, and fourth chemical mixtures to process semiconductor substrates (e.g., single-crystal silicon wafers) and any materials formed thereupon.

Monitoring system 500 further preferably includes supply distribution system 508 and return distribution system 510. Supply distribution system 508 is preferably configured to selectively transport the sample flow of a respective chemical mixture from a respective chemical vessel to sensor 506. Supply distribution system 508 preferably includes supply manifold 509. Supply manifold 509 is preferably configured to selectively place sensor 506 in fluid communication with a particular chemical vessel by selective actuation of its constituent valves. Supply manifold 509 may be connected to the first, second, third, and fourth chemical vessels through piping. Supply manifold 509 preferably includes at least one supply valve for each chemical vessel attached thereto. Supply manifold 509 preferably includes first supply valve 538 (CV1S), second supply valve 540 (CV2S), third supply valve 542 (CV3S), and fourth supply valve 544 (CV4S).

Supply distributions system 508 further preferably includes pump 516, which may be arranged downstream of supply manifold 509. Pump 516 is preferably configured to pump fluid flow to sensor 516. Check valves 518 and 519 may be respectively arranged upstream and downstream of pump 516. Check vales 518 and 519 preferably are configured to prevent fluid backflow.

Monitoring system 500 may further include return distribution system 510. Return distribution system 510 is preferably configured to selectively transport a sample flow of a respective chemical mixture from sensor 506 to a respective chemical vessel or to drain 518. Return distribution system 510 may further include a return manifold 511. Return manifold 511 is preferably arranged downstream of sensor 506, and may be connected to sensor 506 by a return flow line. Return manifold 511 may be connected to the first, second, third, and fourth chemical vessels through piping. Preferably, return manifold 511 may be configured to selectively place sensor 506 in fluid communication with a chemical vessel by selective actuation of its constituent return valves. Return manifold 511 preferably includes first return valve 554 (CV1R), second return valve 556 (CV2R), third return valve 558 (CV3R), and fourth return valve 560 (CV4R). Each return valve may be implemented as a single valve or as a series of valves within return manifold 511.

Monitoring system 500 further preferably includes a purge fluid supply 516. Purge fluid supply 516 preferably includes N2 purge supply 520 and DI purge supply 522. Supply manifold 509 may be configured to be in selective fluid communication with N2 purge supply 520 and DI purge supply 522. To this end, supply manifold 509 preferably includes a N2 purge valve 546 and a DI purge valve 548. N2 purge valve 546 is preferably configured to prevent or permit the flow of nitrogen gas from N2 purge supply 520 to sensor 506. DI purge valve 548 is preferably configured to prevent or permit the flow of deionized water from N2 purge supply to sensor 506.

Monitoring system 500 further preferably includes a drain 518. Return manifold 511 is preferably configured to selectively place sensor 506 in fluid communication with drain 518 such that fluids leaving sensor 506 may be transported to drain 518. Return manifold 511 may include a drain valve 552 configured to prevent or permit fluid flow from sensor 506 to drain 518.

Monitoring system 500 further preferably includes a control system 512. Control system 512 is preferably configured to interface with the various components of monitoring system 500 to direct a monitoring process. Control system 512 preferably includes controller 528. Controller 528 is preferably a programmable controller. Control system 512 also preferably includes display unit 536. Display unit 536 is preferably configured to display sample attribute values transmitted from controller 528. Control system 512 further includes digital output board 532. Digital output board 532 may provide additional digital I/O channels for control system 512. Preferably, controller 528 is configured to send signals to processing tool 526 through digital output board 532. Control system 512 preferably includes auxiliary channel 534. Controller 528 may transmit unfiltered measurements from sensor 506 to auxiliary channel 534 to be logged on another device, such a laptop for onsite analysis. As with monitoring system 200, actions of monitoring system 500 are preferably at least partially directed through software. The programming instructions of the software may be at least temporarily stored within storage element 514 of controller 528.

Each of the above-described components of monitoring system 500 may be configured to perform one or more of the functions that their numerically respective counterparts of monitoring system 200 may be configured to perform (including and in addition to those described in regard to FIG. 12) For example, sensor 506 may be configured to perform one or more of the functions that sensor 206 may be configured to perform, controller 528 may be configured to perform one or more of the functions that controller 228 may be configured to perform, and return manifold 511 may be configured to perform one or more of the functions that return manifold 211 may be configured to perform. Monitoring system 500, however, may also have additional functionality beyond that of monitoring system 200.

Preferably, monitoring system 500 is also capable of implementing process control techniques, and preferably contains additional components beyond those included in monitoring system 200 for accomplishing such ends. For example, monitoring system 500 preferably includes first chemical supply 570 and second chemical supply 572 (FIG. 13). First chemical supply 570 and second chemical supply 572 preferably represent sources of a first chemical and a second chemical, respectively. The first chemical and second chemical are each preferably constituent chemicals of the chemical mixtures monitored by monitoring system 500. In an embodiment in which the first, second, third, and forth chemical mixtures are SC1 mixtures, the first and second chemical supplies may each be any one of water, hydrogen peroxide, or ammonium hydroxide. The first and second chemical supplies may supply pure chemicals or mixtures of chemicals containing the first and second chemicals. First and second chemical supplies 570 and 572 may be configured similarly to first and second chemical supplies 420 and 422, respectively.

Monitoring system 500 may further include a first supply control system 524 and second supply control system 525. First supply control system 524 and second supply control system 525 may be configured similarly to first supply control system 424 and second supply control system 425, respectively. First supply control system 524 preferably is configured to control the amount of the first chemical that is supplied from first chemical supply 572. Likewise, second supply control system 525 is preferably configured to control the amount of the second chemical that is supplied from second chemical supply 572.

First and second supply control systems 524 and 525 are preferably each configured to respectively supply the first and second chemical to the a chemical vessel through return distribution system 510. Preferably, each supply control system is in fluid communication with return manifold 511. Return manifold 511 preferably includes at least one chemical supply valve for each chemical supplied thereto. Preferably, return manifold 511 includes a first chemical supply manifold valve 562 (CS1) and a second chemical supply manifold valve 564 (CS2). First chemical supply valve 562 is preferably configured to prevent or permit the access of a first chemical supply flow from first chemical supply system 524 to a chemical vessel (when the respective return valve for that chemical vessel is open). Likewise, second chemical supply valve 564 is preferably configured to prevent or permit flow the access of a second chemical supply flow from second chemical supply system 525 into a chemical vessel (when the respective return valve for that chemical vessel is open). First chemical supply valve 562 and second chemical supply valve 564 are both preferably solenoid valves, configured to be actuated upon receipt of an appropriate signal, e.g., from control system 512.

First and second supply control systems 524 and 525 may include a variety of devices to respectively control the supply of first and second chemicals. As shown in FIG. 13, first supply control system 524 and second supply control system 525 preferably incorporate a series of valves along an injection line to control the flow of the first and second chemicals, respectively, to return distribution system 510, to be subsequently transported to a desired chemical vessel. First supply control system preferably includes first chemical initial valve 574 (SVI1). First chemical initial valve 574 preferably connects first chemical supply 570 to the injection line of first supply control system 524. First chemical initial valve 574 may be opened to allow flow of the first chemical from first chemical supply 570 to occur. First chemical initial valve 574 is preferably a solenoid valve, configured to be actuated upon receipt of an appropriate signal, e.g., from control system 512.

First chemical supply system 524 preferably includes a first metering valve 578, preferably arranged downstream of first chemical initial valve 578. First metering valve 578 is preferably configured to be adjusted to control the amount of the first chemical that is dispensed when first chemical initial valve 578 is open.

First chemical supply system 524 further preferably includes a first Differential Pressure ("DP") cell 578. First DP cell 578 may be used to determine the flow rate of a first chemical supply flow. The first DP cell preferably transmits an analog output signal to control system 512 representing the flow rate of a first chemical supply flow. In an embodiment, first DP cell generates a 4–20 ma output that becomes an analog input to control system 512 when connected across, e.g., a 500-ohm resistor. The flow rate of the first chemical supply flow is preferably proportional to the square root of the signal transmitted by the first DP cell.

First chemical supply system 524 further preferably includes a first chemical return valve 586(SVR1) and a first chemical supply valve 590 (SVS1). The first chemical return and supply valves are each preferably solenoid valves. First chemical return valve 586 is preferably configured to direct a first chemical supply flow to drain 518 (preferably when "on"). (Alternately, the first chemical return valve may be configured to direct flow back to first chemical supply 570 to be recycled.) When configured in an alternate position, first chemical return valve 586 preferably allows a first chemical supply to pass through to first chemical supply valve 590. First chemical supply valve 590 is preferably configured to selectively allow a first chemical supply flow to pass therethrough on to return manifold 511 (and first chemical supply manifold valve 562).

Similarly, second supply control system 525 preferably includes second chemical initial valve 576 (SVI2). Second chemical initial valve 576 preferably connects second chemical supply 572 to the injection line of second supply control system 525. Second chemical initial valve 576 may be opened to allow flow of the second chemical from second chemical supply 572 to occur. Second chemical initial valve 576 is preferably a solenoid valve, configured to be actuated upon receipt of an appropriate signal, e.g., from control system 512.

Second chemical supply system 525 preferably includes a second metering valve 580, preferably arranged downstream of second chemical initial valve 576. Second metering valve 580 is preferably configured to be adjusted to control the amount of the second chemical that is dispensed when second chemical initial valve 580 is open.

Second chemical supply system 525 further preferably includes a second Differential Pressure ("DP") cell 580. Second DP cell 580 may be used to determine the flow rate of a second chemical supply flow. The second DP cell preferably transmits an analog output signal to control system 512 representing the flow rate of a second chemical supply flow. In an embodiment, second DP cell 580 generates a 4–20 ma output that becomes and analog input to control system 512 when connected across, e.g., a 500-ohm resistor. The flow rate of the second chemical supply flow is preferably proportional to the square root of the signal transmitted by the second DP cell.

Second chemical supply system 525 further preferably includes a second chemical return valve 588 (SVR2) and a second chemical supply valve 592 (SVS2). The second chemical return and supply valves are each preferably solenoid valves. Second chemical return valve 588 is preferably configured to direct a second chemical supply flow to drain 518 (preferably when "on"). (Alternately, the second chemical return valve may be configured to direct flow back to second chemical supply 572 to be recycled.) When configured in an alternate position, second chemical return valve 588 preferably allows a second chemical supply to pass through to second chemical supply valve 592. Second chemical supply valve 592 is preferably configured to selectively allow a second chemical supply flow to pass therethrough onto return manifold 511 (and second chemical supply manifold valve 564). Although as shown in FIGS. 12 and 13 monitoring system 500 may be configured to supply a first and a second chemical, monitoring system 500 may be configured to supply more than two chemicals for use in control processes as needed.

Control system 512 may be further configured to direct one or more control processes. To aid in the implementation of process control techniques, control system 514 may further include an analog-to-digital (A/D) converter 537. A/D converter 537 is preferably configured to convert analog inputs transmitted by first DP cell 582 and second DP cell 584 into digital inputs for use by controller 528. A/D converter 537 may be configured to communicate with controller 228 over a PLCbus interface. Suitable A/D converters include the Z-World XP8500.

Furthermore, control system 512 is preferably configured to execute several sets of programming instructions to direct the operation of one or more control sequences performed by monitoring system 500. The programming instructions may at least temporarily reside in storage element 514. Control system 514 may be configured to execute monitoring process 600 similarly to the manner in which monitoring system 400 may execute monitoring process 600 and in accordance with the above description of the components and sub-components of monitoring system 500. For example, control process 614 may be executed by control system 512 to direct monitoring system 500 to perform a control sequence for an nth bulk attribute in the nth chemical mixture.

Figure 20:
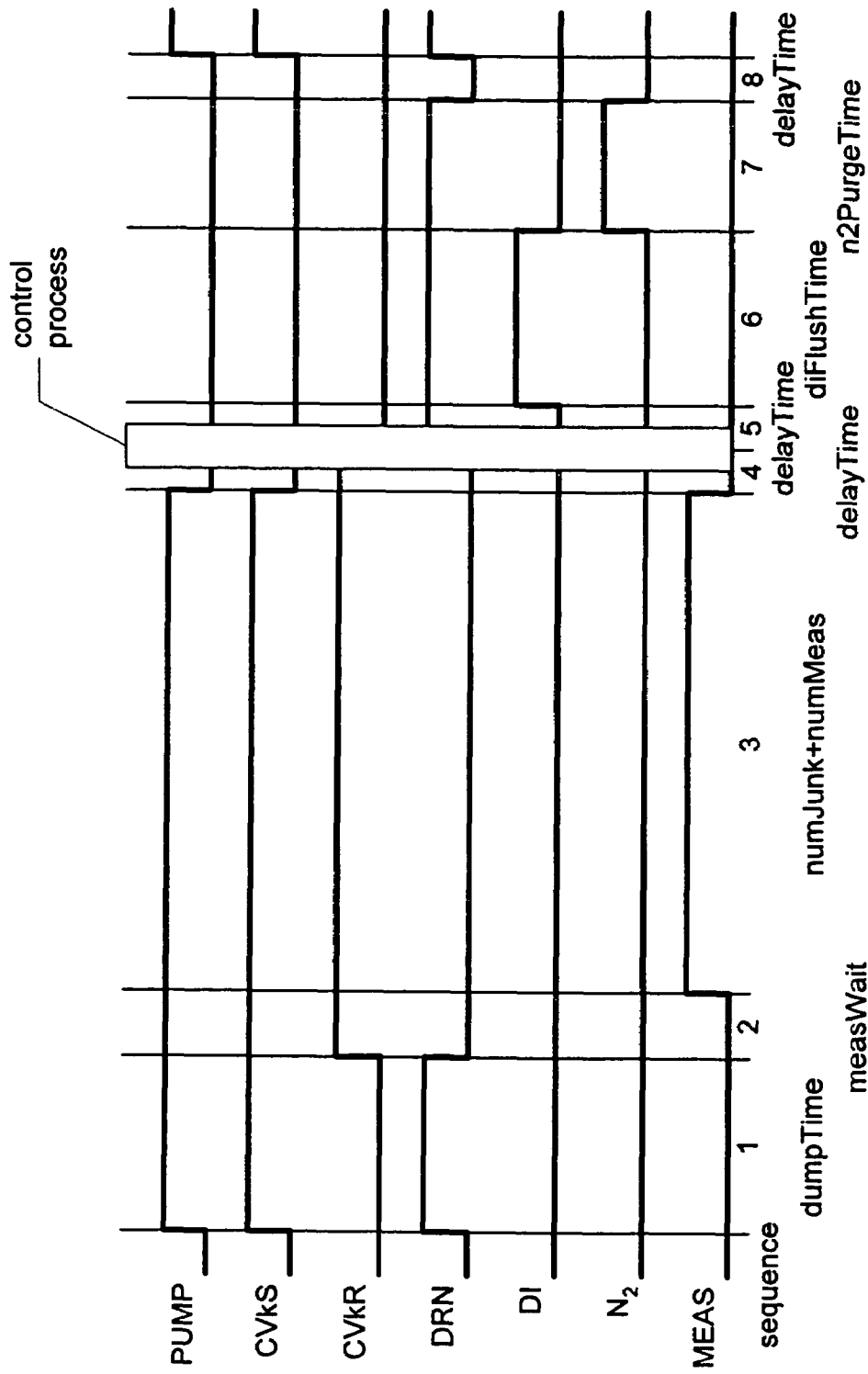
FIG. 20 is a timing diagram showing a sequence of control system outputs during a monitoring process, in which a control loop sequence is executed.
Figure 21:
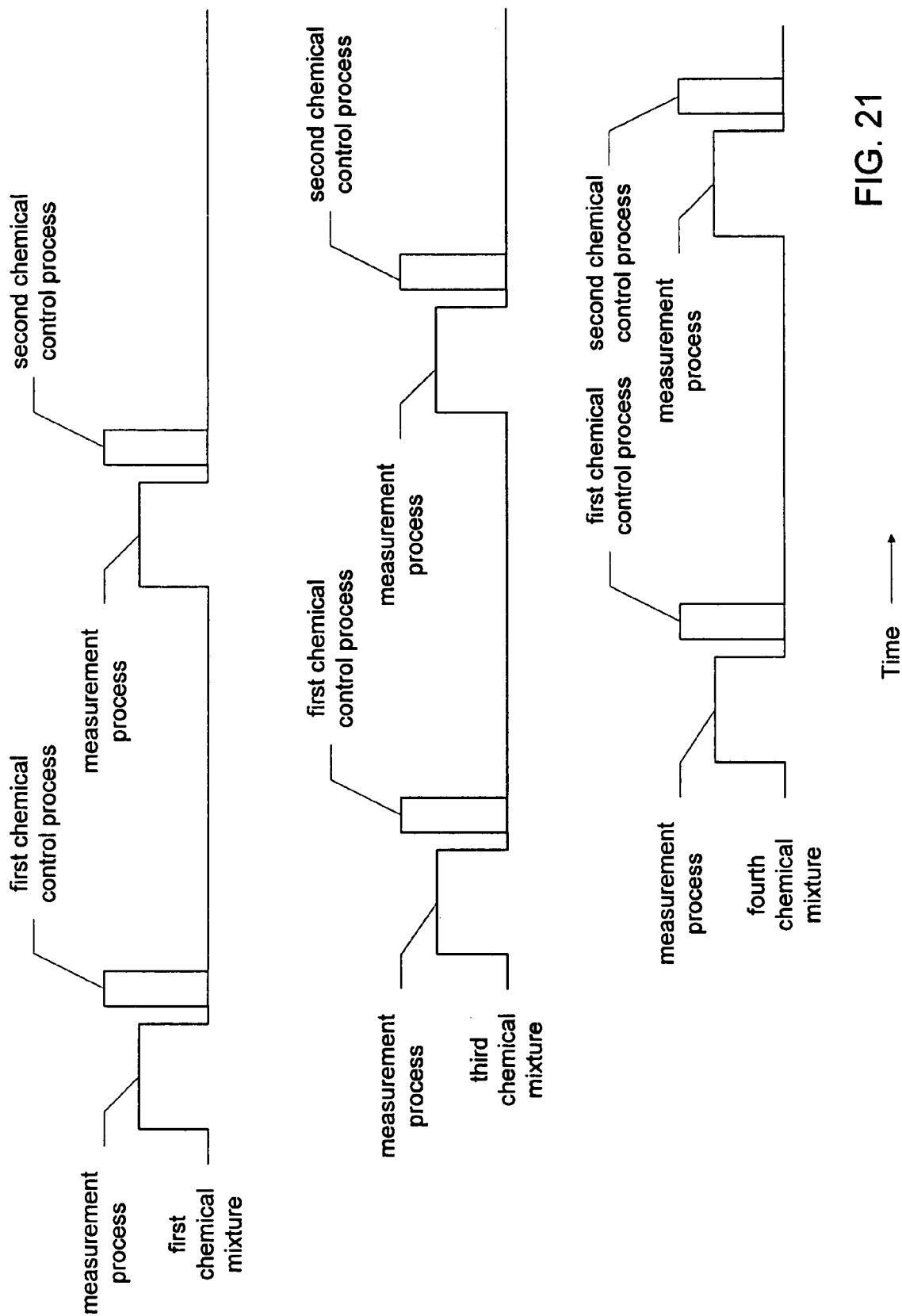
FIG. 21 is a diagram showing a sequence in which control loops for multiple chemical concentrations may be separately executed.
Figure 22:
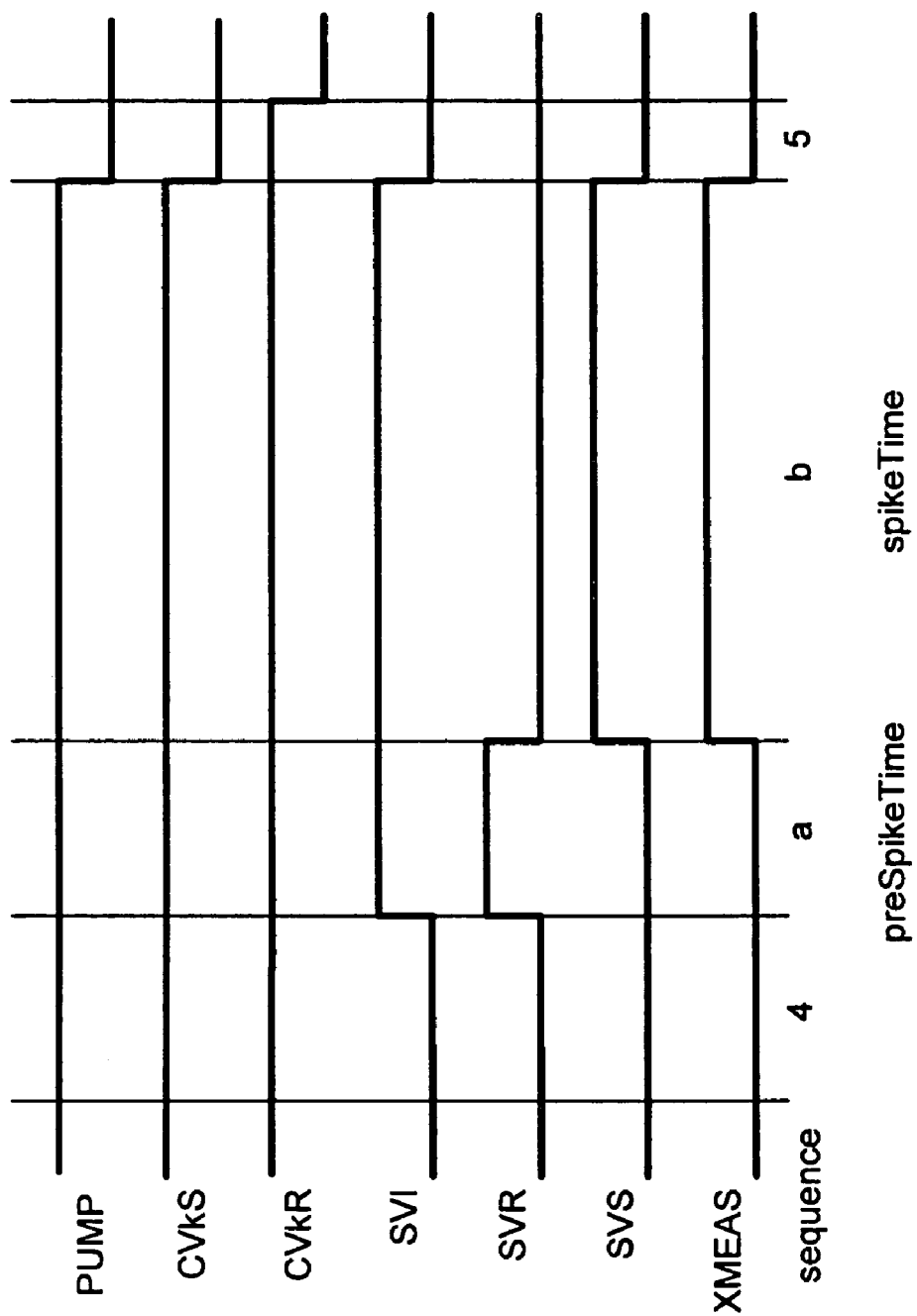
FIG. 22 is a timing diagram showing the control loop sequence executed in the process depicted in FIG. 20.

FIGS. 20–22 may aid in understanding how monitoring system 500 may execute monitoring p 600 in an embodiment. FIG. 20 presents a timing diagram showing the operation of various components of monitoring system 500 during the execution of monitoring process 600 for an nth chemical mixture in accordance with an embodiment. The terms along the y-axis of FIG. 20 may represent potential states of various solenoids driving components and/or sub-processes ("components") of monitoring system 500 at certain points within monitoring process 600. "High" values are intended to show that a particular component is "on", and "low" values are intended to show the particular component is "off".

As shown in FIG. 20, "PUMP" preferably represents the state of pump 516, "CVkS" preferably represents the state of the nth supply valve (e.g., if the second chemical mixture is currently being monitored, then CV2S is the respective supply valve), "CVKR" preferably represents the state of the nth return valve (e.g., if the third chemical mixture is being monitored, then "CV3R" is the respective return valve), "DRN" preferably represents the state of the drain valve 552, "DI" represents the state of DI purge valve 548, and "N2" preferably represents the state of N2 purge valve 546. "MEAS" preferably represents whether control system 512 is actively processing (e.g., accepting and displaying) attribute values measured by sensor 506.

The sequences shown in FIG. 20 for components of monitoring system 500 may be performed in a manner similar to the sequences shown in FIG. 10 for components monitoring system 200. As shown in FIG. 20, however, a control process may be executed between the beginning of sequence 4 and the end of sequence 5. The control process may be control process 614.

FIG. 22 presents a timing diagram showing the operation of various components of monitoring system 500 during the execution of control process 600 for an nth chemical mixture in accordance with an embodiment. The terms along the y-axis of FIG. 22 may represent potential states of various solenoids driving components and/or sub-processes ("components") of monitoring system 500 at certain points within control process 614. "High" values are intended to show that a particular component is "on", and "low" values are intended to show the particular component is "off". FIG. 22 preferably demonstrates the supply of a first chemical to the nth chemical vessel as part of control process 614.

As shown in FIG. 22, "PUMP" preferably represents the state of pump 516, "CVkS" preferably represents the state of the nth supply valve (e.g., if the second chemical mixture is currently being monitored, then CV2S is the respective supply valve), "CVKR" preferably represents the state of the nth return valve (e.g., if the third chemical mixture is being monitored, then "CV3R" is the respective return valve), "SVI" preferably represents the state of the first chemical initial valve 574, "SVR" preferably represents the state of first chemical return valve 586, and "SVS" preferably represents the state of first chemical supply valve 590. "XMEAS" preferably represents whether controller 528 is actively processing (e.g., accepting and displaying) first chemical supply flow rate data transmitted by first DP cell 582.

Control process 614 may be conceptually sub-divided into sequences in which various actions are performed by, e.g., monitoring system 500. Sequences a and b shown in FIG. 22 preferably represent sequences that may be performed after a control response has been generated that dictates that first chemical supply process 634 will be executed to direct a first chemical flow. Additionally, a control response time is preferably calculated in a previous processing step (e.g., processing step 632).

At the beginning of sequence a, first chemical initial valve may be opened to allow a first chemical supply flow to flow from first chemical supply 570. First chemical return valve 586 is preferably also opened at the start of sequence a, and so after passing through first metering valve 578 and first DP cell 582, the first chemical supply flow may be transported to drain 518. The components are preferably maintained in this condition for a preSpikeTime (i.e., a pre-control response time, which may be, e.g., about 3 seconds). This may allow flow to be established in the injection line of first supply system 524.

Then at the beginning of sequence b, first chemical return valve 586 may be closed and first chemical supply valve 590 may be opened. Opening first chemical supply valve 590 preferably allows the first chemical supply flow to flow to return manifold 511 and subsequently into the chemical vessel (by opening the appropriate return valve within the return manifold). In addition, controller 528 may begin processing first chemical flow rate values transmitted by DP cell 582 (indicated by XMEAS going "on"). The components are preferably maintained in this condition for a spikeTime (i.e., a control response time, preferably calculated in processing step 632). After spikeTime has passed, a quantity of the first chemical sufficient to bring the nth bulk attribute at or near the nth attribute setpoint values has been transported to the nth chemical vessel. At the end of sequence b, first chemical supply valve 590 may be closed and controller 528 may cease to process data from first DP cell 528 (indicated by XMEAS going "off"). In addition, pump 516, may be deactivated, and the nth supply valve may be closed.

The process shown in FIG. 22 may be performed in a similar manner to supply a second chemical to the nth chemical vessel by substituting the components of second chemical supply system 525 above where appropriate (e.g., a substitute second chemical initial valve 578 for first chemical initial valve 576 as "SVI")]

As stated above, it may be undesirable to mix chemicals supplied during a control process (e.g., the first and second chemicals). Consequently, when implementing control process 614 on the concentrations of multiple chemicals within an nth chemical mixture, the control processes for each chemical are preferably executed on separate repetitions of monitoring process 600 for each concentration monitored. FIG. 21 shows an example how control processes can be spaced out for multiple chemical concentrations for multiple chemical mixtures. (This is for an embodiment in which second chemical vessel 502 is configured as a spare, so consequently the second chemical vessel is not shown in FIG. 22.)

Further modifications and alternative embodiments of various aspects of the invention will be apparent to those skilled in the art in view of this description. Accordingly, this description is to be construed as illustrative only and is for teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A monitoring system, comprising:
   a first chemical vessel containing a first chemical mixture;
   a second chemical vessel containing a second chemical mixture;
   a sensor configured to selectively receive a first sample flow of said first chemical mixture from said first chemical vessel and to selectively receive a second sample flow of said second chemical mixture from said second chemical vessel, wherein said sensor is configured to measure a first sample attribute of said first sample flow and a second sample attribute of said second sample flow;
   a supply distribution system configured to selectively transport said first sample flow and said second sample flow to said sensor;

a purge fluid supply, wherein said supply distribution system is further configured to selectively transport a purge fluid flow from said purge fluid supply to said sensor;

a drain configured to receive fluids; and a return distribution system wherein said return distribution system is configured to transport purge fluids from said sensor to said drain, and wherein said return distribution system is configured to selectively transport said first sample flow from said sensor to said first chemical vessel or to said drain, and wherein said return distribution system is configured to selectively transport said second sample flow from said sensor to said second chemical vessel or to said drain.

2. The monitoring system of claim 1, wherein said sensor is a concentration sensor configured to measure concentration, and wherein said first sample attribute is a first sample concentration of a first chemical within said first sample flow, and wherein said second sample attribute is a second sample concentration of said first chemical within said second sample flow.

3. The monitoring system of claim 2, wherein said first sample flow comprises a liquid, and wherein said second sample flow comprises a liquid.

4. The monitoring system of claim 1, wherein said supply distribution system is configured to transport said first sample flow and said second sample flow to said sensor at a substantially constant flow rate during operation.

5. A monitoring system 1, comprising:

a first chemical vessel containing a first chemical mixture;

a second chemical vessel containing a second chemical mixture; and a sensor configured to selectively receive a first sample flow of said first chemical mixture from said first chemical vessel and to selectively receive a second sample flow of said second chemical mixture from said second chemical vessel, wherein said sensor is configured to measure a first sample attribute of said first sample flow and a second sample attribute of said second sample flow;

wherein said sensor is configured to measure a first sample attribute value for said first sample attribute and a second sample attribute value for said second sample attribute, and further comprising a control system configured to receive said first sample attribute value and said second sample attribute value from said sensor, and wherein said control system comprises a display unit configured to display said first sample attribute value and said second sample attribute value.

6. The monitoring system of claim 5, wherein said sensor is configured to measure a plurality of first sample attribute values for said first sample flow, and wherein said control system is configured to receive said plurality of first sample attribute values from said sensor and to filter said plurality of first sample attribute signals to produce a filtered first sample attribute value, and wherein said control system is configured to display said filtered first sample attribute value on said display unit, and wherein said sensor is configured to measure a plurality of second sample attribute values for said second sample flow, and wherein said control system is configured to receive said plurality of second sample attribute values from said sensor and to filter said plurality of second sample attribute values to produce a filtered second sample attribute value, and wherein said control system is configured to display said filtered second sample attribute value on said display unit.

7. The monitoring system of claim 5, wherein said control system is configured to determine whether said first sample attribute value is outside of a first sample attribute value range bounded by a low first sample attribute value and a high first sample attribute value, and wherein said control system is configured to generate an out-of-tolerance signal upon determining that said first sample attribute value is outside of said first sample attribute value range.

8. The monitoring system of claim 7, wherein said first sample attribute value range is a primary first sample attribute value range and said low first sample attribute value is a primary low first attribute value, and wherein said high first sample attribute value is a primary high first sample attribute value, and wherein said control system is further configured to determine whether said first sample attribute value is outside of a secondary first sample attribute value range bounded by a secondary low first sample attribute value and a secondary high first sample attribute value, said secondary first sample attribute value range being larger than said primary first sample attribute value range, and further comprising a processing tool configured to use said first chemical mixture in processing a semiconductor substrate, and wherein upon a determination that said first sample attribute value is outside of a secondary first sample attribute value range, said control system is configured to transmit an inhibit signal to said processing tool for said first chemical vessel, and wherein said processing tool is configured to refrain from using said first chemical mixture in processing upon receipt of said inhibit signal for said first chemical vessel.

9. A monitoring system, comprising:

a first chemical vessel containing a first chemical mixture;

a second chemical vessel containing a second chemical mixture; and a sensor configured to selectively receive a first sample flow of said first chemical mixture from said first chemical vessel and to selectively receive a second sample flow of said second chemical mixture from said second chemical vessel, wherein said sensor is configured to measure a first sample attribute of said first sample flow and a second sample attribute of said second sample flow;

wherein said first chemical mixture comprises a first bulk attribute value, and further comprising a control system configured to receive said first sample attribute value and said second sample attribute value from said sensor, wherein said control system is configured to input said first sample attribute value into a first attribute control algorithm to calculate a first attribute control output, and wherein said control system is further configured to direct the adjusting of said first bulk attribute value according to said first attribute control output.

10. The monitoring system of claim 9, wherein said control system is configured to determine a first attribute error value from said first sample attribute value and a first attribute setpoint value, and wherein said first attribute control output comprises a first attribute control response time based on said first sample attribute value, and wherein if said first attribute error value is less than a first attribute dead band value, said control system is configured to set said first attribute control response time to zero, and wherein if said first attribute error value is greater than a first attribute dead band value, said control system is configured to calculate said first attribute control response time from said first attribute error value.

11. The monitoring system of claim 9, wherein said first bulk attribute value is a concentration of a first chemical within said first chemical mixture, and further comprising a first chemical supply configured to be in fluid communication with said first chemical vessel, and wherein said control system is configured to direct the transporting of a first chemical supply flow from said first chemical supply to said first chemical vessel to increase said first chemical concentration within said first chemical mixture.

12. The monitoring system of claim 11, wherein said first chemical mixture further comprise a second chemical having a second chemical concentration within said first chemical mixture, and further comprising a second chemical supply configured to be in fluid communication with said first chemical vessel, and wherein said control system is configured to direct the transporting of a second chemical supply flow from said second chemical supply to said first chemical vessel to decrease said first chemical concentration within said first chemical mixture.

13. The monitoring system of claim 11, wherein said second chemical mixture comprises a first chemical having a first chemical concentration within said second mixture, and wherein said first chemical supply is configured to be in fluid communication with said second chemical vessel, and wherein said control system is configured to direct the transporting of a first chemical supply flow from said first chemical supply to said second chemical vessel to increase said first chemical concentration within said second chemical mixture.

* * * * *

UNITED STATES PATENT AND TRADEMARK OFFICE
CERTIFICATE OF CORRECTION

PATENT NO. : 7,198,753 B1 Page 1 of 1
APPLICATION NO. : 09/366441
DATED : April 3, 2007
INVENTOR(S) : Mark A. Campbell, Phuong-Anh Tang and Gary R. Anderson It is certified that error appears in the above-identified patent and that said Letters Patent is hereby corrected as shown below:

Claim 5, col. 45, line 29, please delete "1," after "A monitoring system".

Signed and Sealed this

Twelfth Day of June, 2007

JON W. DUDAS
*Director of the United States Patent and Trademark Office*